United States Patent
Anissimov et al.

(10) Patent No.: US 7,285,657 B2
(45) Date of Patent: Oct. 23, 2007

(54) **RUBISCO SMALL SUBUNIT PROMOTES FROM *BRASSICA RAPA* AND USES THEREOF**

(75) Inventors: Andrei Anissimov, Helsinki (FI); Seppo Paavo Kaijalainen, Helsinki (FI); Kimmo Koivu, Helsinki (FI); Kari Petri Juntunen, Helsinki (FI); Anne Kanerva, Itasalmi (FI)

(73) Assignee: Unicorp Ltd, Helsinki (FI)

( * ) Notice: Subject to any disclaimer, the term of this patent is extended or adjusted under 35 U.S.C. 154(b) by 0 days.

(21) Appl. No.: 11/433,097

(22) Filed: May 12, 2006

(65) Prior Publication Data

US 2006/0265781 A1    Nov. 23, 2006

Related U.S. Application Data

(62) Division of application No. 10/884,283, filed on Jul. 2, 2004, now Pat. No. 7,115,733.

(60) Provisional application No. 60/484,707, filed on Jul. 3, 2003.

(51) Int. Cl.
  *A01H 1/00*   (2006.01)
  *C07H 21/04*   (2006.01)
  *C12N 5/14*   (2006.01)
  *C12N 15/09*   (2006.01)

(52) U.S. Cl. ......................... 536/24.1; 435/6; 435/91.4; 435/253.3; 435/320.1; 435/468; 435/536; 536/23.1; 800/278; 800/295

(58) Field of Classification Search ..................... None
See application file for complete search history.

(56) References Cited

OTHER PUBLICATIONS

Fiebig et al. (Curr. Genet., 21(2):161-168, 1992).*
Anisimov, A. et al. 2006. Mol Breeding—online publication Nov. 24, 2006 (ISSN: 1380-3743(Print)1572-9788 (online).

* cited by examiner

*Primary Examiner*—Phuong T Bui
*Assistant Examiner*—Vinod Kumar
(74) *Attorney, Agent, or Firm*—Dodds and Associates; Susanne Somersalo; John Dodds

(57) ABSTRACT

The present invention is related to a family of novel spatiotemporally active Rubisco promoters (SEQ ID NO: 1, 2, 3) obtainable from light grown *Brassica* seedlings. Furthermore the invention is related to transgene expression in specific plant organs or at specific stages of plant development. DNA constructs and expression cassettes comprising at least one of the promoter sequences functionally fused in frame with genes encoding desired gene products are disclosed. Seeds from transformed homologous and heterologous plants and from subsequent generation of the transformed plants are collected and used for efficient production of desired gene products, especially in contained conditions.

11 Claims, 19 Drawing Sheets

*RbcS-2-3'UTR-reverse* (SEQ ID NO:25)
TATAACATGCCTCAGAAACAAAAAG

*RbcS-3-3'UTR-reverse* (SEQ ID NO:26)
CGATATAGAATGTCTGAGAAACAGAAAA

*RbcS-4-3'UTR-reverse* (SEQ ID NO:27)
CGATATAGAAAGTCTCGTAACAGAAAT

*RbcS-5-3'UTR-reverse* (SEQ ID NO:28)
CTCAGAAACAAAAATTCAAAAGCA

*RbcS-2-3'UTR-forward* (SEQ ID NO:29)
GGTGCTTAATTCGCGTTGTAA

*RbcS-3-3'UTR-forward* (SEQ ID NO:30)
TGCTTAATTTGCTATGACATTCACAT

*RbcS-4-3'UTR-forward* (SEQ ID NO:31)
CGGTGCTTAATTCGCTTTCATAT

*RbcS-5-3'UTR-forward* (SEQ ID NO:32)
GGCGCTTAATTTTGTTGTCTAAA

Fig. 5

| Brassica plants, transgenic for rbcS-2-GUS | RbcS-2-mRNA | 1.280.000 |
|---|---|---|
| | GUS-mRNA | 387.000 |
| Brassica plants, transgenic for rbcS-4A-GUS | RbcS-4A-mRNA | 25.300.000 |
| | GUS-mRNA | 4.140.000 |

Fig.7

| Construct | Plant | Number of mRNA molecules per a sample (average ± StDev) |
|---|---|---|
| RbcS-4A-HSA | 1 | $9.36 \times 10^6 \pm 3.27 \times 10^6$ |
| | 2 | $1.81 \times 10^6 \pm 4.21 \times 10^5$ |
| | 3 | $2.31 \times 10^6 \pm 1.75 \times 10^6$ |
| | 4 | $1.80 \times 10^6 \pm 3.09 \times 10^6$ |
| RbcS-2-HSA | 1 | $4.37 \times 10^6 \pm 2.15 \times 10^6$ |
| | 2 | $4.97 \times 10^6 \pm 1.44 \times 10^6$ |
| | 3 | $7.00 \times 10^6 \pm 1.53 \times 10^6$ |

Fig. 8

| Days of germination | Total Rubisco mRNA content | Rbcs-4 rubisco mRNA | Rbcs-2 rubisco mRNA | Rbcs-3 rubisco mRNA | Rbcs-5 rubisco mRNA |
|---|---|---|---|---|---|
| 0 | 4712 | ND | 1322 | 66 | 319 |
| 1 | 7123 | 350 | 2692 | 48 | 888 |
| 2 | 366000 | 3530 | 584000 | 101 | 16359 |
| 3 | *14900000* | 1070000 | 9050000 | 4800000 | 258000 |
| 4 | *50300000* | 28700000 | 17900000 | 15900000 | 1440000 |

Fig. 9

| Construct | GUS activity pM / min$^{-1}$ x mg$^{-1}$ | Average value (range) |
|---|---|---|
| RbcS4B-GUS | 272.7 | 243.6 |
| | 291.8 | (174.7 – 291.8) |
| | 174.7 | |
| | 235.3 | |
| 35Sp-GUS | 1060.3 | 2547.4 |
| | 3558.9 | |
| | 3023 | |
| Non-transgenic tobacco | 80.2 | 80.2 |

| Construct | Sample name | mRNA, pg/μg | | mRNA, pg/μg average estimation | |
|---|---|---|---|---|---|
| Rbcs-4-GUS | ND | ND | | ND | |
| Rbcs-4-HSA | T37.2<br>S36.4<br>T33.3<br>S36.3 | 0.95<br>2.11<br>1.21<br>1.18 | | 1.36<br>(0.95 – 2.11) | |
| Rbcs-4-Ab(L+H)-1C2 | | H-chain | L-chain | H-chain | L-chain |
| | S51.16<br>S51.20<br>MF76.32<br>MF76.33<br>MF76.40<br>MF76.41<br>MF76.8 | 2.55<br>13.11<br>9.15<br>18.8<br>20.2<br>3.5<br>5.7 | 0.77<br>3.00<br>ND<br>ND<br>4.2<br>2.95<br>0.54 | 10.43<br>(2.55-20.2) | 1.64<br>(0-4.2) |
| Rbcs-2-GUS | MF65.5<br>MF65.6<br>MF65.7 | 1.42<br>3.08<br>1.72 | | 2.07<br>(1.42-3.08) | |
| Rbcs-2-HSA | More than 10 plants | Not detected or very low expression | | Not detected or very low expression | |
| Rbcs-2-Ab(L+H)-C2 | | H-chain | L-chain | H-chain | L-chain |
| | S56.2<br>S59.3<br>T58.2<br>S59.21<br>S60.8<br>S60.35 | 5.42<br>2.95<br>2.56<br>4.8<br>4.8<br>3.9 | 2.87<br>0.75<br>1.14<br>5.6<br>0.95<br>3.6 | 4.07<br>(2.56-5.42) | 2.49<br>(0.75-5.6) |
| pChry-GUS | T53.4<br>S54.5 | 8.5<br>8.26 | | 8.38 | |
| P.121, P.127 pChry-HSA | T51.2<br>MF68.2<br>MF68.3<br>T51.7<br>MF68.4<br>T51.10 | 3.07<br>0.3<br>0.38<br>0.3<br>0.2<br>1.5 | | 0.96<br>(0.2-3.07) | |
| pChry-Ab(L+H)-1C2 | About 30 samples | Not detected | | Not detected | |

Fig. 12

| Period of germination (hours) | HSA mRNA in Rbcs-4-HSA plants, pg/μg total RNA | HSA mRNA in (Rbcs-2-HSA) x2 plants, pg/μg total RNA | Rubisco mRNA in Rbcs-4-HSA plants, pg/μg total RNA |
|---|---|---|---|
| 12 | 0 | 0 | 0 |
| 24 | 0 | 4.1 | 1.38 |
| 36 | 2.51 | 7.5 | 52.9 |
| 48 | 15.65 | 11.9 | 113.24 |
| 60 | 13 | 7.2 | 117.46 |
| 72 | 20.25 | 12.5 | 113.82 |
| 96 | 21.4 | 7.4 | 108.55 |
| 168 | 16.7 | 6.5 | 99.88 |

Fig. 13

| Transgenic plant species and construct | Transgenic plant species and generation ||||||| 
|---|---|---|---|---|---|---|---|
| | B.n. T0 | B.n. T1 | B.n. T2 | B.n. T3 | C.s. T0 | N.t. T0 | N.t. T1 |
| Rbcs-2-HSA Exp.1 | 0.03 (0.005 – 0.07) | 0.11 | | | | | 0.2 (0.1 – 0.3) |
| Exp.2 | | ND | | | | | 0.214 |
| Exp.3 | | | | | | | 0.53 (0.367 – 0.683) |
| (Rbcs-2-HSA) x 2 Exp.1 | 0.082 | | 0.161 (0.117 – 0.248) | 0.447 (0.34 – 0.62) | 0.967 (0.299 – 3.116) | 0.082 | |
| Exp.2 | | 0.1 | 0.372 | | | 0.035 | |
| Exp.3 | | | 0.18 | | | | |
| Rbcs-4-HSA Exp.1 | 0.021 (0.013 – 0.024) | 0.015 (0.009 – 0.025) | 0.285 | 0.134 | 0.232 (0.18 – 0.291) | 0.115 (0.005 – 0.25) | |
| Exp.2 | | 0.15 | 0.107 (0.08 – 0.199) | 0.179 | 0.676 | 0.41 (0.038 – 3) | |
| Exp.3 | | | 0.183 (0.071 – 0.37) | 0.1 | | | |
| pChry-HSA | | | | | ND | | |

Fig. 14

| Constructs | GUS activity pM/min$^{-1}$ x mg$^{-1}$ Average value (range) |
|---|---|
| RbcS-2(360bp)-GUS | 2301.7 (806.9-5585.3) |
| RbcS-2(624pb)-GUS | 2434.0 (783.8-5806.2) |
| RbcS-2(1.6kb)-GUS | 11095.3 |
| 35Sp-GUS (positive control) | 1460.7 |
| Non-transgenic tobacco | 142.9 |

Quantitative GUS-activity data for transgenic Camelina and tobacco plants

| Constructs | GUS activity pM / min$^{-1}$ x mg$^{-1}$ Average value (range) | |
|---|---|---|
| | Camelina | Tobacco |
| RbcS-2-GUS | 1131 (631-1445) | 4531 (1674-7730) |
| RbcS-4-GUS | 1889 (1091-2768) | 1591 (1512-1669) |
| 35Sp-GUS (positive control) | 231 | 1216 |
| Non-transgenic (negative control) | 113 | 219 |

Fig. 18A

Northern data, obtained from transgenic Camelina and tobacco plants (first regenerants). Data are expressed as mRNA content per 1 µg of total RNA taken into analysis.

| Construct | Camelina, mRNA, pg/µg; average value (range) | Tobacco, mRNA, pg/µg; average value (range) |
|---|---|---|
| Rbcs-2-TNFR-Fc-56UTRshort | 0.6 (one sample available) | No samples available |
| Rbcs-2-TNFR-FcKDEL-56UTRshort | No samples available | 1.0 (one sample available) |
| Rbcs-4-TNFR-Fc-56UTRlong | 3.75 (0.5-10) | No samples available |
| Rbcs-4-TNFR-FcKDEL-56UTRlong | 9.7 (6-13) | No samples available |

Fig. 18B

Fig.19 (codon-optimized HSA gene: coding region plus artificial polyA signal)
AAGCTTGAAGACGACATGAAGTGGGTTACTTTCATCTCTCTTCTTTTCCTTTTCTCTTCT
GCTTACTCTGATGCTCATAAGTCTGAAGTTGCTCATAGATTCAAAGATCTCGGAGAGGAG
AACTTCAAGGCTCTTGTTCTTATCGCTTTCGCTCAGTACCTTCAGCAGTGCCCTTTCGAG
GATCATGTTAAGCTCGTTAACGAGGTTACAGAGTTCGCTAAGACTTGCGTTGCTGATGAG
TCGGCCGAGAACTGCGATAAGTCTCTTCATACTCTTTTCGGAGATAAGCTCTGCACTGTT
GCTACTCTTAGAGAGACTTACGGAGAGATGGCTGATTGCTGCGCTAAGCAGGAGCCTGAG
AGAAACGAGTGCTTCCTTCAACATAAGGATGATAACCCTAACCTTCCTAGACTTGTTAGA
CCTGAGGTTGACGTCATGTGCACTGCTTTCCATGATAACGAGGAGACTTTCCTCAAGAAG
TACCTTTACGAGATCGCTAGAAGGCATCCTTACTTCTACGCTCCTGAGCTTCTTTTCTTC
GCTAAGAGATACAAGGCTGCTTTCACTGAGTGCTGCCAGGCTGCTGATAAGGCTGCATGC
CTTCTTCCTAAGCTCGATGAGCTTAGAGATGAGGGAAAGGCTTCTTCTGCTAAGCAGAGA
CTCAAGTGCGCTAGCCTTCAGAAGTTCGGAGAGAGAGCTTTCAAGGCTTGGGCTGTTGCT
AGACTTTCTCAGAGATTCCCTAAGGCTGAATTCGCTGAAGTTTCTAAGCTCGTTACTGAT
CTTACTAAGGTTCACACTGAGTGCTGCCATGGTGATCTTCTTGAGTGCGCTGATGATAGA
GCTGATCTTGCTAAGTACATCTGCGAGAACCAGGATTCTATCTCTTCTAAACTTAAGGAG
TGCTGCGAGAAGCCTCTTCTTGAAGTCTCATTGCATCGCTGAGGTTGAGAACGATGAG
ATGCCTGCTGATCTTCCTTCTCTTGCTGCAGACTTCGTTGAGTCTAAGGATGTTTGCAAG
AACTACGCTGAGGCTAAGGATGTTTTCCTTGGAATGTTCCTTTACGAGTACGCTAGAAGG
CATCCTGATTACTCTGTTGTTCTTCTTTTGAGACTTGCTAAGACTTACGAGACTACTCTC
GAGAAGTGCTGCGCTGCTGCTGATCCTCATGAGTGCTACGCTAAGGTTTTCGATGAGTTC
AAGCCACTAGTCGAGGAGCCTCAGAACCTTATCAAGCAGAACTGCGAGCTTTTCAAGCAG
CTTGGAGAGTACAAGTTCCAGAACGCTCTTCTTGTTAGATACACTAAGAAGGTTCCACAA
GTTTCTACTCCTACTCTTGTTGAGGTTTCAAGAAACCTTGGAAAAGTTGGATCTAAGTGC
TGCAAGCATCCTGAGGCTAAGAGAATGCCTTGCGCTGAGGATTACCTTTCTGTTGTTCTT
AACCAGCTTTGCGTTCTTCATGAGAAAACACCGGTGTCTGATAGAGTTACTAAGTGCTGC
ACTGAGTCTCTTGTTAACAGAAGGCCTTGCTTCTCTGCTCTTGAAGTTGATGAAACGTAC
GTTCCTAAGGAGTTCAACGCTGAGACTTTCACTTTCCATGCTGATATCTGCACTCTTTCT
GAGAAGGAGAGACAGATCAAGAAGCAGACTGCTCTTGTTGAGCTTGTTAAGCATAAGCCT
AAGGCTACTAAGGAGCAATTGAAGGCTGTTATGGATGATTTCGCTGCTTTCGTTGAGAAG
TGCTGCAAGGCTGATGATAAGGAGACTTGCTTCGCTGAGGAGGGAAAGAAGCTCGTTGCT
GCTTCTCAGGCTGCTCTTGGACTTTTAAGAGCTCTTCGCTTTCATCTAATAATATCTTCTC
*ATTTCATTTCCAATAAGTCTGTTTCTTTTTTTCTCTTTGGATTTCTGTTACGAGACTTTC*
*TATATCGGATTGTAAAATGTCTGATTTTATGAACATGTAATTTCTATATTGCTTCTTCGT*
*CTTGGTTACTTTCCGATGGCTATTAGGTTTTCAACTCTTATTGGGATAAGAAGCCAGTCA*
*AAATAACTTAACAAAACAGGTTAGATAATGTTAGTGGTATATTGTAGAATAAGAAAAGCA*
*GCAAACAGCAGTGGTGACCTCTAGAAGGATCC*

Fig.20 (light chain(anti-hevein 1C2) coding region)
ATGGATTTTCAAGTGCAGATTTTCAGCTTCCTGCTAATCAGTGCCTCAGTCATAATATCC
AGAGGAGAAACGACACTCACGCAGTCTCCATCCTCCCTGTCTGCATCTGTAGGAGACAGA
GTCACCATCACTTGCCGGGCAAGTCAGAGCATTAGCAGCTATTTAAATTGGTATCAGCAG
AAACCAGGGAAAGCCCCTAAGCTCCTGATCTATGCTGCATCCAGTTTGCAAAGTGGGGTC
CCATCAAGGTTCAGTGGCAGTGGATCTGGGACAGATTTCACTCTCACCATCAGCAGTCTG
CAACCTGAAGATTTTGCAACTTACTACTGTCAACAGAGTTACAGTACCCCTCGGACGTTC
GGCCAAGGGACACGACTGGAGATTAAACGTCGAACTGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTTGA Fig.21 (rbcS-4 terminator sequence)
TTCGCTTTCATATAATAATATCTTCTCATTTCATTTCCAATAAGTCTGTTTCTTTTTTC
TCTTTGGATTTCTGTTACGAGACTTTCTATATCGGATTGTAAAATGTCTGATTTTATGAA
CATGTAATTTCTATATTGTTTCTTCTTCGTGGTTACTACTTTCAGATGGCTATTAGGTTT
TCAATTTATTGGGATAAGAAAACAGTCAGAATAATAACTTTACAAAACTGGTTAGATAAG
GTTAGTGGTAATATTTTTTAGAATAGGAAACATTACTACCTACGGAAAAAAATTCATAC
GAAGTTAATTAGTTCATCAAAGATTCAAATAACAAGCACAGTTATAAAAGAAACAAGCAT
TGTATCATTTCATCGTCACATTGACATAGATTTCAAGCATACAGTAGTAGTCATCATTTG
ATATTTGATGTTTCACACTCATCATATGCAGTTTCTGAGATCGTATACATACTATTGGTG
CATTATAATTGCAAATAA Fig.22 (heavy chain (anti-hevein 1C2) coding region)
ATGGAATGGAGTTGGATATTTCTCTTTCTCCTGTCAGGAACTGCAGGTGTCCACTCTCAG
ATCACCTTGAAGGAGTCTGGTCCTACGCTGGTGAAACCCACACAGACCCTCACGCTGACC
TGTAACCTCTCTGGGTTCTCGCTCAGCACCAGCGGAGTGGGTGTGGGCTGGATCCGTCAG
CCCCCAGGAAAGGCCCTGGAGTGGCTCGCACTCATTTATTGGGATGATGATAAGCGCTAC
AGTCCATCTCTGAGGAACAGACTCACCATCACCAAGGACACATCCAAAAACCAGGTGGTC
CTTACAATGACCAACATGGACCCTGTGGACACAGGCACATATTTCTGTGCACGCAGTGTC
AATTATGATGACGTTTCGGGGACTTATCACAGCCACAACTGGTTCGACCCCTGGGGCCAG
GGAACCCTGGTCACCGTCTCCTCATCCACCAAGGGCCCATCGGTCTTCCCCCTGGCACCC
TCCTCCAAGAGCACCTCTGGGGGCACAGCGGCCCTGGGCTGCCTGGTCAAGGACTACTTC
CCCGAACCGGTGACGGTGTCGTGGAACTCAGGCGCCCTGACCAGCGGCGTGCACACCTTC
CCGGCTGTCCTACAGTCCTCAGGACTCTACTCCCTCAGCAGCGTGGTGACCGTGCCCTCC
AGCAGCTTGGGCACCCAGACCTACATCTGCAACGTGAATCACAAGCCCAGCAACACCAAG
GTGGACAAGAGAGTTGAGCCCAAATCTTGTGACAAAACTCACACATGCCCACCGTGCCCA
GCACCTGAACTCCTGGGGGGACCGTCAGTCTTCCTCTTCCCCCCAAAACCCAAGGACACC
CTCATGATCTCCCGGACCCCTGAGGTCACATGCGTGGTGGTGGACGTGAGCCACGAAGAC
CCTGAGGTCAAGTTCAACTGGTACGTGGACGGCGTGGAGGTGCATAATGCCAAGACAAAG
CCGCGGGAGGAGCAGTACAACAGCACGTACCGTGTGGTCAGCGTCCTCACCGTCCTGCAC
CAGGACTGGCTGAATGGCAAGGAGTACAAGTGCAAGGTCTCCAACAAAGCCCTCCCAGCC
CCCATCGAGAAAACCATCTCCAAAGCCAAAGGGCAGCCCCGAGAACCACAGGTGTACACC
CTGCCCCCATCCCGGGAGGAGATGACCAAGAACCAGGTCAGCCTGACCTGCCTGGTCAAA
GGCTTCTATCCCAGCGACATCGCCGTGGAGTGGGAGAGCAATGGGCAGCCGGAGAACAAC
TACAAGACCACGCCTCCCGTGCTGGACTCCGACGGCTCCTTCTTCCTCTATAGCAAGCTC
ACCGTGGACAAGAGCAGGTGGCAGCAGGGGAACGTCTTCTCATGCTCCGTGATGCATGAG
GCTCTGCACAACCACTACACGCAGAAGAGCCTCTCCCTGTCCCCGGGTAAATGA Fig.23 (signal sequence (69nt) plus TNFR part (489 nt))
ATGGCGCCCGTCGCCGTCTGGGCCGCGCTGGCCGTCGGACTGGAGCTCTGGGCTGCGGCG
CACGCCTTG*CCCGCCCAGGTGGCATTTACACCCTACGCCCCGGAGCCCGGGAGCACATGC*
*CGGCTCAGAGAATACTATGACCAGACAGCTCAGATGTGCTGCAGCAAATGCTCGCCGGGC*
*CAACATGCAAAAGTCTTCTGTACCAAGACCTCGGACACCGTGTGTGACTCCTGTGAGGAC*
*AGCACATACACCCAGCTCTGGAACTGGGTTCCCGAGTGCTTGAGCTGTGGCTCCCGCTGT*
*AGCTCTGACCAGGTGGAAACTCAAGCCTGCACTCGGGAACAGAACCGCATCTGCACCTGC*
*AGGCCCGGCTGGTACTGCGCGCTGAGCAAGCAGGAGGGGTGCCGGCTGTGCGCGCCGCTG*
*CGCAAGTGCCGCCCGGGCTTCGGCGTGGCCAGACCAGGAACTGAAACATCAGACGTGGTG*
*TGCAAGCCCTGTGCCCCGGGGACGTTCTCCAACACGACTTCATCCACGGATATTTGCAGG*
*CCCCACCAGATCTGTGAG*

Fig.24 (*Arabidopsisis VSP1* (vegetative storage protein-1 gene) part and rbcS-4-terminator part)
TTAAGCATCTATCTTCATGGCATTGTCCCCTTGTATCCATTTCATATCTATGTCGTTTCG
TTTATCTTTGTAGCCGTTTTGGCACCACTGCTTAAATAAAATGCCAATCCTATCATAACT
CAATAAGTACAACGACTTCGTACTAAATTTTGTTTTTCGTTAAAGGGATCATTAATCAAG
TTTCCATGAAATG*ATGAACATGTAATTTCTATATTGTTTCTTCTTCGTGGTTACTACTTT*
*CAGATGGCTATTAGGTTTTCAATTTATTGGGATAAGAAAACAGTCAGAATAATAACTTTA*
*CAAAACTGGTTAGATAAGGTTAGTGGTAATATTTTTTTAGAATAGGAAACATTACTACCT*
*ACGGAAAAAAATTCATACGAAGTTAATTAGTTCATCAAAGATTCAAATAACAAGCACAGT*
*TATAAAAGAAACAAGCATTGTATCATTTCATCGTCACATTGACATAGATTTCAAGCATAC*
*AGTAGTAGTCATCATTTGATATTTGATGTTTCACACTCATCATATGCAGTTTCTGAGATC*
*GTATACATACTATTGGTGCATTATAATTGCAAATAA*

SEQUENCE LISTING

```
<160> NUMBER OF SEQ ID NOS: 32

<210> SEQ ID NO 1
<211> LENGTH: 2175
<212> TYPE: DNA
<213> ORGANISM: Brassica rapa
<220> FEATURE:
<221> NAME/KEY: misc_feature
<222> LOCATION: (1)..(2175)
<223> OTHER INFORMATION: RbcS-4A

<400> SEQUENCE: 1
gtttcctgag tgttgcacct cctcagtctg agccgtatta agttcaaacc aaactgccgc        60
ttctgctcta gctttactca ggactgaaac cgaggagtag tgtatcttct caaaagccag       120
accatttctc gccttccata gatgccagag tatccaagga aaaaacatcg tatcgctatc       180
ttttggagac ttcctactca tttccaggag atgatataaa cctgccaccg ggagtttgat       240
cgaggacctt tcccaagtgt ccttcgccat ggggcaagaa aaaagtagat ggcagatcga       300
ttcaatacca ccattacata ctttgcaagc agagtctact tgaataccto tactacgaag       360 acgttccatg accgctaaag ccccagagag agctttccaa aggaaatgct taattttggg       420
aggagcacgg atcttccaca gagatttcca aaggtatttc tccaggggag gaagagaagt       480
tgaaatgcta ccatcttcct caggaagcga atcgacaaat ctttaaccac tccgtgatgt       540
```

```
gtagattcca tcttttgtga agccccactt ataaccatct tcctgcatcc tatttggctt      600
caagcgaagg atgatctcag catcatgatc agtaaacgtt cttctcacaa gagctgcatc      660
ccaggcagaa gagttaggga gcagcaggtc tgagattgtc agcgtcagat caatgacact      720
atcctgtctg tagttaggag tcctcggtat agggtcgata atccaattca cgtgccacac      780
attagaactc ctaccattac caatgtctct aatcaaacct tgctcagca gctctctacc      840 atgtaaaatg cttcgccatg catatgacgg cctcgaacct aaactgcttt gcaagaagtc      900
attgtttgca aagtatctac ttttgaggat tcgagccacc agagagttgg ggttattcat      960
gatcctccat gcttgcttag ccaagaaagt taagattagt gataacgatc agctagcgaa     1020
gaaagttaag attagtgatt agaactacgt aatcacctgt cacatttagc tggccttttc     1080
tgtattctaa tatttttaa aatgaaatta tcaacagaaa aaagatattt taaattctta      1140
ataaaatgaa attattttc tgacccgctc tggccttgac ctctataaat atttgagccg       1200
gtgctatgtt caagttctt ttcggtcagc ttgcgtctgc atagtgcata tgatggaagg       1260 atttttggt ggtacatgct ctcggcggtg tagaagcttg cagaagagtt gatgaaattt       1320
gagtcatcac tagcggattc agtgacgtaa atgaggtgat gacgtagctg aaccaattac     1380
gcgtgacatt tcgtagggag acgcgtattg gtgatataaa ttcttaaaac tacaagtgtt     1440
agagtatgtt taatagggag ttcttaaggt gtggttctta aacatgatt atcgatggtg      1500 ggaggagggt ttttacgcgt ggacccctcc atctttttgc aaacaccgtg tttcaatgtc     1560
cccaaataaa aaatgtttca cagaggtttg ttgtactgtt tatggatctc acagacacgt     1620
agcgacttgc gattcatttt tttttttttt tttttaaat ttaagaaacc caaaagtgtt      1680
tttaccgata atcatgctct tagttcttag cgttttagt taaaagttaa aagacagatt      1740
tttatattcc gttaaaaatc cttcattaag cctgcagtaa ttttctttt tgtgtgcaac      1800 tacaagtggt agcaaattaa tgtaactttc tttcacggcg ttgattgttg ggccgattat     1860
gtaccacacg atctcatcct tatgggctct acgaaaagtt gacccacgaa ataaggaag      1920 gagcctaaag catcggctca agtggagacc agaccagtaa ccatacgttt tcataatacg    1980
ataagataag ataacgtttc tgtcacgtgg cattttcatt gtggtcaagt atcgagataa    2040
gggtatcaac accgttcata atcctgtggc tgttaacgac gatatcatga aatatccata    2100
agggttctca ctctatatag atgaccaaag caatagacta acagtaagag ttaagagaag    2160
gaagaagaag tagtc                                                     2175

<210> SEQ ID NO 2
<211> LENGTH: 1016
<212> TYPE: DNA
<213> ORGANISM: Brassica rapa
<220> FEATURE:
<221> NAME/KEY: misc_feature
<222> LOCATION: (1)..(1016)
<223> OTHER INFORMATION: RbcS-4B

<400> SEQUENCE: 2
aacccgaacc gaatccgatc cgataaaaat gaatccgaac cgatccgaat ccgacataaa       60
taccgaatgg atcctgtttt ttggtatttt gggttatggg tattatccga accgaacccg      120
gacctaaatg gatatccgat agaacccgaa acatttaaaa tcacaaaaag aacttctacc      180
aaatatgatc ataattctta atatgtatcc aaaatacttt aagatattat tgaacttcta      240
aaataattat atgttacatg aaggttgatg gtggaatgtg gcggttgatg cctgaagttt      300
```

-continued

```
ttaggttttg gttttgtttt tattgaataa tgtttctcat ttcatgagaa cttattttt      360 gttttatgat ttcatttatc tggttttctt tctatcacta actatgttta tattttgctt     420
gattttgaat gatcacgttt gatgtttttt cttattttg aatcgatttt acttatgttt      480
tggctattaa aatatgtaca aatcatgtat tttaaattcg aagaaccgat ttcatttatg     540
ttttagttac aaaataggta caaatcagat attttaaac caaagaaccg attgggaccc      600
gaacccgaaa gtacaatgag ttataccggt tctttgaaga tttactaacc ccgacccgaa     660
cccgatagaa cccgaaccgg tcccgaaccg aactttata taacccgaat ggggttgatt      720
ttgataaacc cgaaaaaccg aaacccgaat ggataaaacc gaaacccgat tgggaccccg     780
aatgcccatg cctaccagta accatgcgtt ttcataatac gataagataa gataacgttt     840
ctgtcacgtg gcattttcat tgtggtcaag tatcgagata agggtatcaa caccgttcat     900
attcctgtgg ctgttaacga cgatatcatg aaatatccat aagggttctc actctatata     960
gatgaccaaa gcaatagact aacagtaaga gttaagagaa ggaagaagaa gtagtc        1016
```

<210> SEQ ID NO 3
<211> LENGTH: 1651
<212> TYPE: DNA
<213> ORGANISM: Brassica rapa
<220> FEATURE:
<221> NAME/KEY: misc_feature
<222> LOCATION: (1)..(1651)
<223> OTHER INFORMATION: RbcS-2

<400> SEQUENCE: 3

```
ccctttccg tcataagttt tatatatata aaaacatatt tgcccttctt atctccctca       60
tctctctctc tctctctctc tctctctctc tctctctctc tctctctctc tctctccctc     120
tctctctctc tctctctctc tcatccggcg agtgtaaaca tatataacta ttaaattaat    180
ttagaaaaca aactgtttaa tatagccaaa atgaacgtg gggttttagt tgtaaaacaa      240
aaaaaccata ctaactcaaa tctgaacaca ccgtatttt cttgatgttg aattaccact     300
tgatttgtca atttttaccaa aggaatccct caaaattgta actcaaatgt aatacattat    360
acatcaaaaa gtaactcaaa aatctaaaaa ctaatcttac atttaaccca aacttaatct    420
tataacacat tgcttttaat gtaagtatga ttttttggat taataacttt tacattcatt    480
aaaaaaatca taaaaaatac aacactatct gaccagagct aaatataatt tgtaatcttg    540
tatcattgcg atagaggcat ccgaaatttc atttaattga aagttcggt tcggttcagc      600 atgttatata aaaaaatggt ttttggctcg ttctgttcgg taatcggtta gatcggtttc    660 aaaaaaaaatt tgttcccaaa tttcaatccg aactaaccta gctaaccaaa acttcgaatc    720
gaagtaacca agctacctaa aattactcaa aattttgaac cgaactaaca gaattaacca    780
aaacattgga ccgaattaac caattttacc caattttta accgaaatat aatcagaacc    840
aaaaacttaa gttagtttcg gtaaaatttt aaaaactgaa ctacccaaat accaaactga    900
actgaatttt ttatgttc gacaagattt tagtcgaacc gaactacctg aatccgcagg      960
aagttaccca tcagagagag atgcacaaag cattacctaa aaacgttaca tttagtgttt    1020
tggtaccact tttattgatt tttttttttg acagctattg atttagttta tagttttaa    1080 ctattaagta acagttttgtt tttcgtgtca aaaaaaaag taacagtttt tatacggttt    1140 tactttttaac ttaccaatcg gacccactat tcttttgttt tgttggttt gaatatggac    1200 atgaccatta cagtagtatc attactcata agttaattag tacgcatac atgtataatt    1260 caagtacatc tcgtatagta atttcaattg tgaatttaat aatgaaccta atcaaattaa    1320
```

```
gcgaaactaa ttcatataaa tagaaggtcc gcgaacattg aaatgtagat catgcgtcag    1380
aattgtcctc tctcagtagg aaggagccaa aagcattggc tcaagttgag acgagtaacc    1440
atacacattc atacgttttc ttacaagata agataagata atgttatttc tcacccttc     1500 tttaatacct gtggcagtta acgacgatat catgaaatca tgatccttcg atcattaggg    1560
ctttatacct cttgcgcttc tcactatata tagataacca agcaataga caaacaagta     1620 agttaagaga aaagaagaag aagaagtagt a                                   1651
```

<210> SEQ ID NO 4
<211> LENGTH: 42
<212> TYPE: DNA
<213> ORGANISM: artificial sequence
<220> FEATURE:
<223> OTHER INFORMATION: primer e3a

<400> SEQUENCE: 4

```
caucaucauc aucaaccgtc aagtccagtg catcagtttc at                         42
```

<210> SEQ ID NO 5
<211> LENGTH: 27
<212> TYPE: DNA
<213> ORGANISM: artificial sequence
<220> FEATURE:
<223> OTHER INFORMATION: primer atu

<400> SEQUENCE: 5

```
cuacuacuac uattttttt ttttttt                                           27
```

<210> SEQ ID NO 6
<211> LENGTH: 48
<212> TYPE: DNA
<213> ORGANISM: artificial sequence
<220> FEATURE:
<223> OTHER INFORMATION: adapter

<400> SEQUENCE: 6

```
gtaatacgac tcactatagg gcacgcgtgg tcgacggccc gggctggt                   48
```

<210> SEQ ID NO 7
<211> LENGTH: 8
<212> TYPE: DNA
<213> ORGANISM: artificial sequence
<220> FEATURE:
<223> OTHER INFORMATION: adapter

<400> SEQUENCE: 7

```
accagccc                                                                8
```

<210> SEQ ID NO 8
<211> LENGTH: 22
<212> TYPE: DNA
<213> ORGANISM: artificial sequence
<220> FEATURE:
<223> OTHER INFORMATION: adapter primer AP1

<400> SEQUENCE: 8

```
gtaatacgac tcactatagg gc                                               22
```

<210> SEQ ID NO 9
<211> LENGTH: 34
<212> TYPE: DNA
<213> ORGANISM: artificial sequence
<220> FEATURE:

```
<223> OTHER INFORMATION: UTR2-specific L1 primer

<400> SEQUENCE: 9
ggccacactt gacaatccga tataacatgc ctca                          34

<210> SEQ ID NO 10
<211> LENGTH: 19
<212> TYPE: DNA
<213> ORGANISM: artificial sequence
<220> FEATURE:
<223> OTHER INFORMATION: AP2 primer

<400> SEQUENCE: 10
actatagggc acgcgtggt                                           19

<210> SEQ ID NO 11
<211> LENGTH: 23
<212> TYPE: DNA
<213> ORGANISM: artificial sequence
<220> FEATURE:
<223> OTHER INFORMATION: UTR2-specific L2 primer

<400> SEQUENCE: 11
caaatggaaa tgaaatgagg tag                                      23

<210> SEQ ID NO 12
<211> LENGTH: 30
<212> TYPE: DNA
<213> ORGANISM: artificial sequence
<220> FEATURE:
<223> OTHER INFORMATION: RbcS-RN

<400> SEQUENCE: 12
acccgggccc aggagagcat agaggaagcc                               30

<210> SEQ ID NO 13
<211> LENGTH: 30
<212> TYPE: DNA
<213> ORGANISM: artificial sequence
<220> FEATURE:
<223> OTHER INFORMATION: RbcS-R1

<400> SEQUENCE: 13
ctgtgaatgg agcaaccatg gccgcttgag                               30

<210> SEQ ID NO 14
<211> LENGTH: 30
<212> TYPE: DNA
<213> ORGANISM: artificial sequence
<220> FEATURE:
<223> OTHER INFORMATION: RbcS-R2

<400> SEQUENCE: 14
ctgtgaatgg agcaaccatg gccgcttgag                               30

<210> SEQ ID NO 15
<211> LENGTH: 2132
<212> TYPE: DNA
<213> ORGANISM: artificial sequence
<220> FEATURE:
<223> OTHER INFORMATION: codon-optimized Human Serum Albumin (HSA) gene

<400> SEQUENCE: 15
aagcttgaag acgacatgaa gtgggttact ttcatctctc ttcttttcct tttctcttct    60
gcttactctg atgctcataa gtctgaagtt gctcatagat tcaaagatct cggagaggag   120
```

```
aacttcaagg ctcttgttct tatcgctttc gctcagtacc ttcagcagtg cccttcgag      180 gatcatgtta agctcgttaa cgaggttaca gagttcgcta agacttgcgt tgctgatgag      240
tcggccgaga actgcgataa gtctcttcat actcttttcg gagataagct ctgcactgtt      300
gctactctta gagagactta cggagagatg gctgattgct gcgctaagca ggagcctgag      360
agaaacgagt gcttccttca acataaggat gataaccccta accttcctag acttgttaga      420
cctgaggttg acgtcatgtg cactgctttc catgataacg aggagacttt cctcaagaag      480
tacctttacg agatcgctag aaggcatcct tacttctacg ctcctgagct tcttttcttc      540
gctaagagat acaaggctgc tttcactgag tgctgccagg ctgctgataa ggctgcatgc      600
cttcttccta agctcgatga gcttagagat gagggaaagg cttcttctgc taagcagaga      660
ctcaagtgcg ctagccttca agaagttcgga gagagagctt tcaaggcttg ggctgttgct      720
agactttctc agagattccc taaggctgaa ttcgctgaag tttctaagct cgttactgat      780
cttactaagg ttcacactga gtgctgccat ggtgatcttc ttgagtgcgc tgatgataga      840
gctgatcttg ctaagtacat ctgcgagaac caggattcta tctcttctaa acttaaggag      900
tgctgcgaga agcctcttct tgagaagtct cattgcatcg ctgaggttga aacgatgag       960 atgcctgctg atcttccttc tcttgctgca gacttcgttg agtctaagga tgtttgcaag     1020
aactacgctg aggctaagga tgttttcctt ggaatgttcc tttacgagta cgctagaagg     1080
catcctgatt actctgttgt tcttcttttg agcttgcta agacttacga gactactctc      1140
gagaagtgct gcgctgctgc tgatcctcat gagtgctacg ctaaggtttt cgatgagttc     1200
aagccactag tcgaggagcc tcagaacctt atcaagcaga actgcgagct tttcaagcag     1260
cttggagagt acaagttcca gaacgctctt cttgttagat acactaagaa ggttccacaa     1320
gtttctactc ctactcttgt tgaggtttca agaaaccttg gaaaagttgg atctaagtgc     1380
tgcaagcatc ctgaggctaa gagaatgcct tgcgctgagg attacctttc tgttgttctt     1440
aaccagcttt gcgttcttca tgagaaaaca ccggtgtctg atagagttac taagtgctgc     1500
actgagtctc ttgttaacag aaggccttgc ttctctgctc ttgaagttga tgaaacgtac     1560
gttcctaagg agttcaacgc tgagactttc actttccatg ctgatatctg cactctttct     1620
gagaaggaga gacagatcaa gaagcagact gctcttgttg agcttgttaa gcataagcct     1680
aaggctacta aggagcaatt gaaggctgtt atggatgatt cgctgctttt cgttgagaag     1740
tgctgcaagc tgatgataa ggagacttgc ttcgctgagg agggaaagaa gctcgttgct     1800
gcttctcagg ctgctcttgg actttaagag ctcttcgctt tcatctaata atatcttctc     1860
atttcatttc caataagtct gtttctttt ttctcttttgg atttctgtta cgagactttc      1920
tatatcggat tgtaaaatgt ctgattttat gaacatgtaa tttctatatt gcttcttcgt     1980
cttggttact ttccgatggc tattaggttt tcaactctta ttgggataag aagccagtca     2040
aaataactta acaaaacagg ttagataatg ttagtggtat attgtagaat aagaaaagca     2100
gcaaacagca gtggtgacct ctagaaggat cc                                   2132
```

<210> SEQ ID NO 16
<211> LENGTH: 714
<212> TYPE: DNA
<213> ORGANISM: artificial sequence
<220> FEATURE:
<223> OTHER INFORMATION: light chaing (anti-hevein 1C2) coding region
<220> FEATURE:
<221> NAME/KEY: misc_feature
<222> LOCATION: (1)..(66)

<223> OTHER INFORMATION: sequence coding for mouse signal peptide
<220> FEATURE:
<221> NAME/KEY: misc_feature
<222> LOCATION: (67)..(324)
<223> OTHER INFORMATION: light chain antihevein 1C2 antigen variable
      region
<220> FEATURE:
<221> NAME/KEY: misc_feature
<222> LOCATION: (325)..(714)
<223> OTHER INFORMATION: kappa light chain constant region

<400> SEQUENCE: 16

```
atggattttc aagtgcagat ttcagcttc ctgctaatca gtgcctcagt cataatatcc      60
agaggagaaa cgacactcac gcagtctcca tcctccctgt ctgcatctgt aggagacaga    120
gtcaccatca cttgccgggc aagtcagagc attagcagct atttaaattg gtatcagcag    180
aaaccaggga agcccctaa gctcctgatc tatgctgcat ccagtttgca aagtggggtc    240
ccatcaaggt tcagtggcag tggatctggg acagatttca ctctcaccat cagcagtctg    300
caacctgaag attttgcaac ttactactgt caacagagtt acagtacccc tcggacgttc    360
ggccaaggga cacgactgga gattaaacgt cgaactgtgg ctgcaccatc tgtcttcatc    420
ttcccgccat ctgatgagca gttgaaatct ggaactgcct ctgttgtgtg cctgctgaat    480
aacttctatc ccagagaggc caaagtacag tggaaggtgg ataacgccct ccaatcgggt    540
aactcccagg agagtgtcac agagcaggac agcaaggaca gcacctacag cctcagcagc    600
accctgacgc tgagcaaagc agactacgag aaacacaaag tctacgcctg cgaagtcacc    660
catcagggcc tgagctcgcc cgtcacaaag agcttcaaca ggggagagtg ttga          714
```

<210> SEQ ID NO 17
<211> LENGTH: 498
<212> TYPE: DNA
<213> ORGANISM: Brassica rapa
<220> FEATURE:
<221> NAME/KEY: terminator
<222> LOCATION: (1)..(498)
<223> OTHER INFORMATION: rbcS-4 terminator

<400> SEQUENCE: 17

```
ttcgctttca tataataata tcttctcatt tcatttccaa taagtctgtt tcttttttc      60 tctttggatt tctgttacga gactttctat atcggattgt aaaatgtctg atttatgaa    120 catgtaattt ctatattgtt tcttcttcgt ggttactact ttcagatggc tattaggttt    180
tcaatttatt gggataagaa aacagtcaga ataataactt acaaaactg gttagataag    240 gttagtggta atattttttt agaataggaa acattactac ctacggaaaa aaattcatac    300
gaagttaatt agttcatcaa agattcaaat aacaagcaca gttataaaag aaacaagcat    360
tgtatcattt catcgtcaca ttgacataga tttcaagcat acagtagtag tcatcatttg    420
atatttgatg tttcacactc atcatatgca gtttctgaga tcgtatacat actattggtg    480
cattataatt gcaaataa                                                  498
```

<210> SEQ ID NO 18
<211> LENGTH: 1434
<212> TYPE: DNA
<213> ORGANISM: artificial sequence
<220> FEATURE:
<223> OTHER INFORMATION: heavy chain (anti-hevein 1C2) coding region
<220> FEATURE:
<221> NAME/KEY: misc_feature
<222> LOCATION: (1)..(57)
<223> OTHER INFORMATION: a sequence coding for mouse signal peptide
<220> FEATURE:

<221> NAME/KEY: misc_feature
<222> LOCATION: (58)..(387)
<223> OTHER INFORMATION: heavy chain anti-hevein 1C2 antigen variable
      region
<220> FEATURE:
<221> NAME/KEY: misc_feature
<222> LOCATION: (445)..(990)
<223> OTHER INFORMATION: igG heavy chain constant region
<220> FEATURE:
<221> NAME/KEY: misc_feature
<222> LOCATION: (445)..(990)
<223> OTHER INFORMATION: IgG1 heavy chain constant region

<400> SEQUENCE: 18

```
atggaatgga gttggatatt tctctttctc ctgtcaggaa ctgcaggtgt ccactctcag     60
atcaccttga aggagtctgg tcctacgctg gtgaaaccca cacagaccct cacgctgacc    120
tgtaacctct ctgggttctc gctcagcacc agcggagtgg gtgtgggctg gatccgtcag    180
cccccaggaa aggccctgga gtggctcgca ctcatttatt gggatgatga taagcgctac    240
agtccatctc tgaggaacag actcaccatc accaaggaca catccaaaaa ccaggtggtc    300
cttacaatga ccaacatgga ccctgtggac acaggcacat atttctgtgc acgcagtgtc    360
aattatgatg acgtttcggg gacttatcac agccacaact ggttcgaccc ctggggccag    420
ggaaccctgg tcaccgtctc ctcatccacc aagggcccat cggtcttccc cctggcaccc    480
tcctccaaga gcacctctgg gggcacagcg gccctgggct gcctggtcaa ggactacttc    540
cccgaaccgg tgacggtgtc gtggaactca ggcgccctga ccagcggcgt gcacaccttc    600
ccggctgtcc tacagtcctc aggactctac tccctcagca gcgtggtgac cgtgccctcc    660
agcagcttgg gcacccagac ctacatctgc aacgtgaatc acaagcccag caacaccaag    720
gtggacaaga gagttgagcc caaatcttgt gacaaaactc acacatgccc accgtgccca    780
gcacctgaac tcctgggggg accgtcagtc ttcctcttcc ccccaaaacc caaggacacc    840
ctcatgatct cccggacccc tgaggtcaca tgcgtggtgg tggacgtgag ccacgaagac    900
cctgaggtca agttcaactg gtacgtggac ggcgtggagg tgcataatgc caagacaaag    960
ccgcgggagg agcagtacaa cagcacgtac cgtgtggtca gcgtcctcac cgtcctgcac   1020
caggactggc tgaatggcaa ggagtacaag tgcaaggtct ccaacaaagc cctcccagcc   1080
cccatcgaga aaaccatctc caaagccaaa gggcagcccc gagaaccaca ggtgtacacc   1140
ctgcccccat cccgggagga gatgaccaag aaccaggtca gcctgacctg cctggtcaaa   1200
ggcttctatc ccagcgacat cgccgtggag tgggagagca atgggcagcc ggagaacaac   1260
tacaagacca cgcctcccgt gctggactcc gacggctcct tcttcctcta tagcaagctc   1320
accgtggaca gagcaggtg gcagcagggg aacgtcttct catgctccgt gatgcatgag   1380
gctctgcaca accactacac gcagaagagc ctctccctgt ccccgggtaa atga         1434
```

<210> SEQ ID NO 19
<211> LENGTH: 558
<212> TYPE: DNA
<213> ORGANISM: artificial sequence
<220> FEATURE:
<223> OTHER INFORMATION: signal sequence and TNFR
<220> FEATURE:
<221> NAME/KEY: misc_feature
<222> LOCATION: (1)..(69)
<223> OTHER INFORMATION: signal sequence
<220> FEATURE:
<221> NAME/KEY: misc_feature
<222> LOCATION: (70)..(489)
<223> OTHER INFORMATION: TNFR sequence

```
<400> SEQUENCE: 19
atggcgcccg tcgccgtctg ggccgcgctg ccgtcggac tggagctctg ggctgcggcg      60
cacgccttgc cgcccaggt ggcatttaca ccctacgccc cggagcccgg gagcacatgc    120
cggctcagag aatactatga ccagacagct cagatgtgct gcagcaaatg ctcgccgggc    180
caacatgcaa agtcttctg taccaagacc tcggacaccg tgtgtgactc ctgtgaggac    240
agcacataca cccagctctg gaactgggtt cccgagtgct tgagctgtgg ctcccgctgt    300
agctctgacc aggtggaaac tcaagcctgc actcgggaac agaaccgcat ctgcacctgc    360
aggcccggct ggtactgcgc gctgagcaag caggaggggg gccggctgtg cgcgccgctg    420
cgcaagtgcc gcccgggctt cggcgtggcc agaccaggaa ctgaaacatc agacgtggtg    480
tgcaagccct gtgccccggg gacgttctcc aacacgactt catccacgga tatttgcagg    540
ccccaccaga tctgtgag                                                 558

<210> SEQ ID NO 20
<211> LENGTH: 576
<212> TYPE: DNA
<213> ORGANISM: artificial sequence
<220> FEATURE:
<223> OTHER INFORMATION: Arabidobsis VSP1 (vegetative storage protein)
      and a part of rbcS-4 terminator
<220> FEATURE:
<221> NAME/KEY: misc_feature
<222> LOCATION: (1)..(226)
<223> OTHER INFORMATION: Arabidopsis VSP1
<220> FEATURE:
<221> NAME/KEY: misc_feature
<222> LOCATION: (227)..(576)
<223> OTHER INFORMATION: a part of rbcS-4 terminator

<400> SEQUENCE: 20
ttaagcatct atcttcatgg cattgtcccc ttgtatccat ttcatatcta tgtcgtttcg      60
tttatctttg tagccgtttt ggcaccactg cttaaataaa atgccaatcc tatcataact    120
caataagtac aacgacttcg tactaaattt tgttttcgt taaagggatc attaatcaag    180
tttccatgaa atgatgaaca tgtaatttct atattgtttc ttcttcgtgg ttactacttt    240
cagatggcta ttaggttttc aatttattgg gataagaaaa cagtcagaat aataacttta    300
caaaactggt tagataaggt tagtggtaat attttttag aataggaaac attactacct    360
acggaaaaaa attcatacga agttaattag ttcatcaaag attcaaataa caagcacagt    420
tataaaagaa acaagcattg tatcatttca tcgtcacatt gacatagatt tcaagcatac    480
agtagtagtc atcatttgat atttgatgtt tcacactcat catatgcagt ttctgagatc    540
gtatacatac tattggtgca ttataattgc aaataa                             576

<210> SEQ ID NO 21
<211> LENGTH: 1149
<212> TYPE: DNA
<213> ORGANISM: Brassica rapa
<220> FEATURE:
<221> NAME/KEY: misc_feature
<222> LOCATION: (1)..(1149)
<223> OTHER INFORMATION: rbcS-1

<400> SEQUENCE: 21
ctggtaattc tgttttaata acactgtcat gaaaactgaa ttcataggtt tctccaggcc      60
gtagatagtg gaagcctaga tcgtcgtcgt tagatataca attaatccttc aagatattgt    120 ttcgaccaag agagttctta aagtgcacgg agttttttc attccacttt gcgttactca    180
```

```
aacctatgca caatccaata gtgagaagaa acacgagag acgattcatt gtgttgatta      240
tttgtaatgg ccttcttcta tagttctttt aaatttagaa gtaatccgta gataaccaag      300
agggaagatg tgtaatatat atatatatag tggcgttaca cggataagca ctcattttt      360 ctctattttt aaacatcttt gttttgacta atattaagaa aacgttgatc gcttttacta      420
tttttcgtgt ccttatcccg tgttgctgtt ttgcatctat ttaaagagta gatgctatag      480
tttttttacg gcttagacta gatgcttttg gtaatttgtt tcagtgttca gctttgaccc      540
cctttttttg gtgtaaatgt taaaattcag ccttcagctt tgacctttgt gatattatat      600
gaatgactgt gtttatgtaa aatttattga tttataaaac tcttaagaaa aactatatta      660
ataaaaaata gaattgttac tcttcttcgt ttgagtatga acataatcat caatagtgct      720
ctcatcactc ataagttata actaatgacg acattacatg tctgattcaa gtaatttaat      780
tttcttgtag tacaggtcca cgaagattta aatgtaggtc atgcgtctca tttctttct      840 gccaaaagga aggagccaag agaatcggct caagtggaca ctagtaacca tacacattca      900
ctcattacct tccaagaaaa gataagataa gaaaattttc tgccacgtgg ccttatcata      960
gtggtctgta tcgataaggg tgtcaacacc tttccttaat cctgtggcag gtaacgacgt     1020
tatcatcaga catgaatccc gcactctttg atctaagggc tttatgcctc atgccgtcct     1080
cactatatat agatgaccaa aggaatagac aaacaagtaa gtaagagaaa agagaaaaaa     1140
gaagtagta                                                             1149
```

```
<210> SEQ ID NO 22
<211> LENGTH: 877
<212> TYPE: DNA
<213> ORGANISM: Brassica rapa
<220> FEATURE:
<221> NAME/KEY: misc_feature
<222> LOCATION: (1)..(877)
<223> OTHER INFORMATION: RbcS-3

<400> SEQUENCE: 22
```

```
ctggtgattc tattttaata gattaaatat tattctttag aagacgaagc atgagatcga       60
tgacaacgca atgctcattt catctggttt ttctgtcctt gcctcaattg gttactgtta      120
cagatgttaa taaatgagta attaccaata ggataccta agttttcca aactttcaaa       180 cccaaaactt actctatttg acttaagagc atttctaaga gcaatgttac ttttagagca      240
tttctaagag caatgttact tttaaagttt agtgaacttt aaatttgagg tttaagagca      300
tgtccaatgg ttagaagaca gacttacagt ttaactaccg tgttcagtta ccaatcgggc      360
ccactatata atattgtttc ccttcttcgt ttatcgacgt tagcattaac agtgtactcc      420
ttgctcacaa ctaagtagct cataacttgt aatagttata atactaaatg tgatcttatt      480
aattaactga atcaaactaa gccaatagtt aggagttcca ctaacattaa agagtaggcc      540
atgtgtttga tttgtcgtct cccaatagga aggaaccaaa agcatcggct caagtggagg      600
ccagcagtaa atcagtaacc atatatacac acattcatac attttaatgc aagataagat      660
aatagcattt ctgccacgtg gccttaacat agtggtcagt atcgataagg gtctcaacac      720
cttctcttaa tcatgtggca gttaacgacg ttatcatgaa atctggaccc tctggttatt      780 agggccttt cctcttgcgg ttctcgttat atatagataa ccaaagcgat agacaaacaa      840
gtaagttaag agaaaagaag aagaagaaga agtagta                             877
```

```
<210> SEQ ID NO 23
<211> LENGTH: 904
```

```
<212> TYPE: DNA
<213> ORGANISM: Brassica rapa
<220> FEATURE:
<221> NAME/KEY: misc_feature
<222> LOCATION: (1)..(904)
<223> OTHER INFORMATION: RbcS-5

<400> SEQUENCE: 23
gtcgacaaaa ctcttctttt atgtcgcagg atggtccgaa tgagacaata acaccttcca      60
tccttctgat gaggtcacat attcaatcat gtcagttaaa gtcacatatc catgcgatgc     120
gaatgcagct tgcttcgtct caatgtatta aatacgaatc agactgtatt gttcctactt     180
gatgacagag tcaacatact tttcccaaag catgggcgtg acgtcgtcac gtagatcgca     240
ttattgtctt ttatcatata atgaaccggg ctacctttat ctttgggttt ttgaatttgt     300
tgggctcttt atagaatcgg atcgggcatt gatgagagtg tgaagtccac ctccaacaaa     360
aactcttgaa ctataactaa tgatgtcctt gtattattag tgataacttt tctaagtaat     420
gtattgtgga aaattacatg tttgattcaa atcatttcct tattaataat taaatattga     480
ttgagaacta actaaccgaa tcgatgtaca tgccaaactg aatcttacac aattgaacat     540
aagttcaaac cattaaaagt aggtcaggtt ctgattcttt tttcaattgg aaggagtcaa     600
aagcatgact caagtggaca ccagtaacca tacacattca ctcattccct cacaagaaac     660
gataagataa tggaattttc tgccacgtgg ccttatcata gtggtctgta ttgataaggg     720
tgtcaacacc tttccttaat cctgtggcag gcaacgacgt tatcatgaat cttggaccca     780
tttattacta gggcttttg tctcttgccg ttctcactat ataaagatga ccaaagcaat     840
agacaagcaa gtaaaagaaa ggagaaaaag aagaagaaga agaagagaag aactagtaca     900
cgta                                                                  904

<210> SEQ ID NO 24
<211> LENGTH: 12
<212> TYPE: DNA
<213> ORGANISM: artificial sequence
<220> FEATURE:
<223> OTHER INFORMATION: KDEL signal; chemically synthesized

<400> SEQUENCE: 24
aaagacgagc tg                                                          12

<210> SEQ ID NO 25
<211> LENGTH: 25
<212> TYPE: DNA
<213> ORGANISM: artificial sequence
<220> FEATURE:
<223> OTHER INFORMATION: RbcS-2- 3'UTR-reverse

<400> SEQUENCE: 25
tataacatgc ctcagaaaca aaaag                                            25

<210> SEQ ID NO 26
<211> LENGTH: 28
<212> TYPE: DNA
<213> ORGANISM: artificial sequence
<220> FEATURE:
<223> OTHER INFORMATION: rbcS-3-3'UTR-reverse

<400> SEQUENCE: 26
cgatatagaa tgtctgagaa acagaaaa                                         28

<210> SEQ ID NO 27
```

```
<211> LENGTH: 27
<212> TYPE: DNA
<213> ORGANISM: artificial sequence
<220> FEATURE:
<223> OTHER INFORMATION: RbcS-4-3' UTR-reverse

<400> SEQUENCE: 27
cgatatagaa agtctcgtaa cagaaat                                    27

<210> SEQ ID NO 28
<211> LENGTH: 24
<212> TYPE: DNA
<213> ORGANISM: artificial sequence
<220> FEATURE:
<223> OTHER INFORMATION: RbcS-5-3' UTR-reverse

<400> SEQUENCE: 28
ctcagaaaca aaaattcaaa agca                                       24

<210> SEQ ID NO 29
<211> LENGTH: 21
<212> TYPE: DNA
<213> ORGANISM: artificial sequence
<220> FEATURE:
<223> OTHER INFORMATION: RbcS-2-3'UTR-forward

<400> SEQUENCE: 29
ggtgcttaat tcgcgttgta a                                          21

<210> SEQ ID NO 30
<211> LENGTH: 26
<212> TYPE: DNA
<213> ORGANISM: artificial  sequence
<220> FEATURE:
<223> OTHER INFORMATION: Rbc-3-3' UTR-forward

<400> SEQUENCE: 30
tgcttaattt gctatgacat tcacat                                     26

<210> SEQ ID NO 31
<211> LENGTH: 23
<212> TYPE: DNA
<213> ORGANISM: artificial sequence
<220> FEATURE:
<223> OTHER INFORMATION: RbcS-4-3' UTR-forward

<400> SEQUENCE: 31
cggtgcttaa ttcgctttca tat                                        23

<210> SEQ ID NO 32
<211> LENGTH: 23
<212> TYPE: DNA
<213> ORGANISM: artificial sequence
<220> FEATURE:
<223> OTHER INFORMATION: RbcS-5-3' UTR forward

<400> SEQUENCE: 32
ggcgcttaat tttgttgtct aaa                                        23
```

RUBISCO SMALL SUBUNIT PROMOTES FROM *BRASSICA RAPA* AND USES THEREOF

CROSS REFERENCE TO RELATED APPLICATIONS

This non-provisional patent application is a divisional application of the U.S. non provisional application Ser. No. 10/884,283 filed as Jul. 2, 2004, now U.S. Pat. No. 7,115,733, which claims priority of provisional patent application No. 60/484,707 filed on Jul. 3, 2003.

SEQUENCE DATA

This application contains sequence data provided on a computer readable diskette and as a paper version. The paper version of the sequence data is identical to the data provided on the diskette.

BACKGROUND OF THE INVENTION

1. Field of the Invention

The present invention relates generally to transgenic plants. More specifically, it relates to transgene expression at a specific stage of plant development. Even more specifically the invention relates to novel Rubisco promoters of *Brassica* species, and DNA constructs or expression cassettes comprising at least one of the promoters for transformation of homologous or heterologous plants for efficient production of gene products, particularly for contained use.

2. Description of Related Art

Assimilation and conversion of atmospheric carbon dioxide via the reaction with ribulose-1,5-bisphosphate into phosphoglycerate strictly depends on the activity of Rubisco enzyme. Structurally it consists of eight small subunits (SSU) and eight large subunits (LSU). The SSU proteins are encoded by several genes located in plant nuclear genome, while LSU genes are found in plastid genome. The number of Rubisco SSU genes in different plants varies from four copies up to fifteen copies or more in some polyploid genomes. There are at least four copies of Rubisco SSU genes in *Arabidobsis thaliana* and twelve or even more copies in wheat.

Based on their structure and function these nuclear genes may form multigenic families. The structure of these families is extensively studied, for example, in *Arabidopsis* and tomato plants. In tomato there are five Rubisco SSU (rbcS) genes located in three chromosomal loci, one of these genes being situated in chromosome 3, and the other four in chromosome 2. Moreover, three of the genes are known to be organized in tandem array within a 10 kb region. The same situation is known to occur in *Arabidopsis thaliana* rbcS gene family.

In *Brassica napus* coding sequences, 5' and 3' regulatory regions of three rbcS genes have been cloned and sequenced (accession numbers X75334, X55937, X61097). It has been suggested that *Brassica napus* contains no more than three rbcS genes.

There are also cDNA sequences obtained from mRNA of *Brassica napus* rbcS genes (one of them has been published with accession number X07367).

There have also been attempts to clarify the fine structure of the promoters of *Brassica napus* rbcS genes. Essential regulatory elements, like TATA, G-, $G^S$, and I-boxes, necessary for basic activity and light regulation of the promoters has been described, and also putative silencer elements in one of the promoters has been studied.

Clearly, however the information available on gene structure and activity does not enable identification of differently expressing members of *Brassica* rbcS gene family in different plant tissues or development stages and under various environmental conditions.

Transgenic plants are used increasingly for production of various desired proteins and other gene products. An important aspect in designing transgenic plants is how to obtain significant levels of transgene expression in desired plant tissues or at desired plant development phases. The role of promoters is essentially important in this aspect and there is a clear need for new plant promoters.

Outchkourov et al. (2002) cloned an abundantly transcribed rbcS1 of the Rubisco small-subunit gene family of *Chrysanthemum* species (*Chrysantemum morifolium* Ramat.). Outchkourov et al. showed that tobacco plants transformed with a gene cassette containing uidA gene under the control of rbsS1-promoter provided β-glucuronidase (GUS) levels up to 10% of total soluble proteins in the leaves.

Even if the *Chrysanthemum* Rubisco promoter cloned by Outchkourov et al. gives high protein expression levels in tobacco leaves it may not fit for purposes where protein production is needed at a specific stage of development, such as protein production in seedlings or in germinating seeds.

Plant seeds and cotyledons are particularly advantageous for production because at early cotyledon development, nutritional sources from seeds, including amino acids and oils are abundantly available as raw material for de novo protein synthesis. Additionally, the recovery of the expressed gene products from homogenized sprouts is easier and more efficient than from harvested leaves. Production of transgenic proteins in germinating seeds is an approach that can be realized in contained manner in a suitable laboratory. For such purposes a promoter being active during seed germination or cotyledon development is essential and the published rbcS promoters are not applicable.

For purposes of producing transgenic expression products in developing sprouts there is a need for promoters expressing strongly at late stages of cotyledon development, because then the leaf size of cotyledons is bigger than at early cotyledon development and the material needed for compound collection is easier and more efficient to harvest.

Moreover, another important prerequisite for foreign protein production in plant tissues is high expression level of the proteins, and therefore there is a clear need for new promoters giving high protein content at a specific development stage and/or in a specific organ of a plant.

A promoter, which is active during seed germination or cotyledon development, is of particular importance in the production of transgene products in contained conditions in a suitable laboratory. None of the rbcS promoters so far published are however applicable for said purpose in *Brassicaceae* plants. New promoters for different new applications are therefore clearly needed.

SUMMARY OF THE INVENTION

The present invention provides a solution for the problems encountered by industry seeking for plant promoters giving high expression rates and being specific for a certain development stage or a certain organ.

An objective of the present invention is to obtain a spatiotemporally targeted high expression level of desired gene product or protein.

The present invention provides new rbcS promoters, which are obtainable from a selection of rbcS gene sequences identified by their abundant expression in light-grown cotyledons of *Brassica rapa* species.

The present invention provides new promoters according to SEQ ID NO: 1, SEQ ID NO: 2 and SEQ ID NO: 3.

The present invention provides fusion constructs comprising new promoters functionally linked to reporter genes. The promoters used in the expression cassettes, and whole constructs provide both homologous and heterologous systems, which are useful for transforming homologous and heterologous plants and confer the capacity of efficient production of homologous and heterologous proteins.

The present invention provides transgenic seedlings of various plant species for production of foreign proteins and peptides.

Furthermore, the present invention provides transgenic *Camelina* plants, particularly *Camelina sativa* plants producing high levels of desired proteins in germinating seedlings.

The present invention provides transgenic plants producing high levels of gene products encoded by naturally isolated genes or synthetic or semisynthetic genes in germinating seedlings. Such gene products may, for example, be Human Serum Albumin (HSA), antibodies and medically active proteins.

The DNA constructs or cassettes are used for transforming host plants, which are exemplified by *Brassica* and *Camelina* species. The transformed zero generation plant comprises one or more of the expression cassettes according to the present disclosure and seeds of the zero generation plants may be used for providing further generations of transgenic plants but the seeds may also be used directly for production of the desired gene products in the seedlings during seed germination and cotyledon development.

Therefore, the present invention is also related to transformed plants, subsequent generations thereof as well as seeds and seedlings carrying at least one expression cassette having at least one of the novel promoters.

The present invention also discloses a method for producing further promoters having properties which are substantially similar to those of the family of Rubisco promoters disclosed here. The method comprises the step of evaluating the expression in light grown seedlings, identifying the most highly expressed genes and selecting from said genes promoters having the capability to direct gene expression into developing cotyledons.

BRIEF DESCRIPTION OF THE DRAWINGS

FIG. 2A illustrates alignments of cloned *Brassica rapa* rbcS promoters Global DNA alignment. Reference molecule rbcS-1-300nt (SEQ ID NO:21). Alignment of proximal 300 bp of rbcS-2-300nt (SEQ ID NO:3), rbcS-3-300nt (SEQ ID NO:22); rbcS-4A-300nt (SEQ ID NO:1) and rbcS-5-300nt (SEQ ID NO:23) is shown. Scoring matrix: Linear (Mismatch 2, OpenGAp 4m ExtGap 1). Sequence view: Similarity Format, Color areas of high matches at the same base position.

FIG. 2B illustrates alignments of cloned *Brassica rapa* rbcS-4A (SEQ ID NO: 1) and rbcS-4B promoters (SEQ ID NO: 2) promoters, in which the horizontal boxes represent homologous regions. Alignment of –267 to +33 nt regions of the two sequences is shown. Global DNA alignment. Scoring matrix: Linear (Mismatch 2, OpenGAp 4m ExtGap 1). Sequence view: Similarity Format, Color areas of high matches at the same position.

FIG. 2C illustrates alignments of promoters (upper part) and 3'UTRs (two lowermost alignments) of *Brassica rapa* rbcS -2 and *B. napus* rbcS (X61097). Global DNA alignment. rbcS-2 sequence is according to SEQ ID NO:2. rbcS-23'UTR is according to SEQ ID NO:36, rbcS of *B. napus* is according to SEQ ID NO:33 and 3'UTR sequence of *B. napus* is according to SEQ ID NO:34. Scoring matrix: Linear (Mismatch 2, OpenGAp 4m ExtGap 1). Sequence view: Similarity Format, Color areas of high matches at the same base position.

FIG. 3 illustrates alignments of 1 kb sequences of Rbcs-4A promoter (SEQ ID NO: 1) (upper line) and *Brassica napus* Rubisco promoter published with accession number X61097 (lower line) (SEQ ID NO:33). The sequences show 52% dissimilarity.

FIG. 4 illustrates alignment of 1kb sequences of rbcS-4A promoter (SEQ ID NO: 1) (upper line) and *Chrysanthemum* rbcS1 promoter (lower line) published with accession number AY163904 (SEQ ID NO:35). The sequences show 57% dissimilarity FIG. 5 illustrates sequences of the forward and reverse primers, specific for unique parts of different rubisco 3'UTR types. The primers show that it is possible to discriminate between the different 3'UTR species in real-time PCR. Forward primers are divided in two parts (underlined italics and bold): the left part of each primer corresponds to the last few nucleotides of relevant Rubisco coding regions, and the right part corresponds to specific 3'UTR sequence. All the reverse primers anneal to specific 3'UTR regions. All the amplicon sizes vary in 80 to 100 nt rage.

FIG. 7 demonstrates the amount of mRNA from rbcS-2, rbcS-4 and uidA (encoding β-glucuronidase, GUS) using real-time PCR in transgenic *Brassica* plants transformed with rbcS-2-GUS and rbcS-4A-GUS (Rubisco promoter sequences SEQ ID NO: 3 and SEQ ID NO: 1, respectively).

FIG. 8 illustrates real-Time PCR data indicating the amount of human serum albumin (HSA) specific mRNA molecules in RNA samples of transgenic tobacco plants transformed with rbcS-4A-HSA and rbcS-2-HSA.

FIG. 9 illustrates Real-Time PCR data of the expression levels of different Rubisco promoters in *Brassica napus* seeds, germinated for various times (0 to 4 days). Data represents numbers of molecules per a sample (100 ng of total RNA).

FIG. 12 illustrates Northern data, showing HSA mRNA content in transgenic *Camelina* plants.

FIG. 13 illustrates HSA mRNA content in germinating seeds of transgenic *Brassica napus* plants at various times.

FIG. 14 illustrates the amount of HSA protein in transgenic *Brassica napus* (B.n.), *Camelina sativa* (C.s.) and tobacco plants (N.t.) calculated as % TSP (total soluble protein). Averages with minimum and maximum values are presented.

FIG. 18A illustrates quantitative GUS-activity data for transgenic *Camelina* and tobacco plants transformed with rbcS-2-GUS or rbcS-4-GUS constructs. Plants transformed with 35S-GUS are used as positive controls.

FIG. 18B illustrates Northern blot data, obtained from transgenic *Camelina* and tobacco plants carrying TNFR-constructs. Rbcs-2-TNFR-Fc-56UTRshort contains rbcS-2 (SEQ ID NO: 3) promoter, TNFR part (489 nt) (SEQ ID NO: 19), linked to the part of IgG1 heavy chain constant region ($C_H2+C_H3$ domains), and part of terminator sequence from natural rbcS-4 gene (0,5 kb length). Rbcs-2-TNFR-FcK-DEL-56UTRshort is the same construct, but there is also KDEL signal (12 nt) (SEQ ID NO: 24) after the Fc region (just before STOP codon). Rbcs-4-TNFR-Fc-56UTRlong contains rbcS-4A (SEQ ID NO: 1) promoter, TNFR part (SEQ ID NO: 19), linked to the part of IgG1 heavy chain constant region ($C_H2+C_H3$ domains), and full terminator sequence from natural rbcS-4 gene (2 kb in length). Rbcs-4-TNFR-FcKDEL-56UTRlong is the same as previous construct, but there is also KDEL signal (12 nt) (SEQ ID NO: 24) after the Fc region Oust before STOP codon).

DETAILED DESCRIPTION OF THE INVENTION

Figure 1:
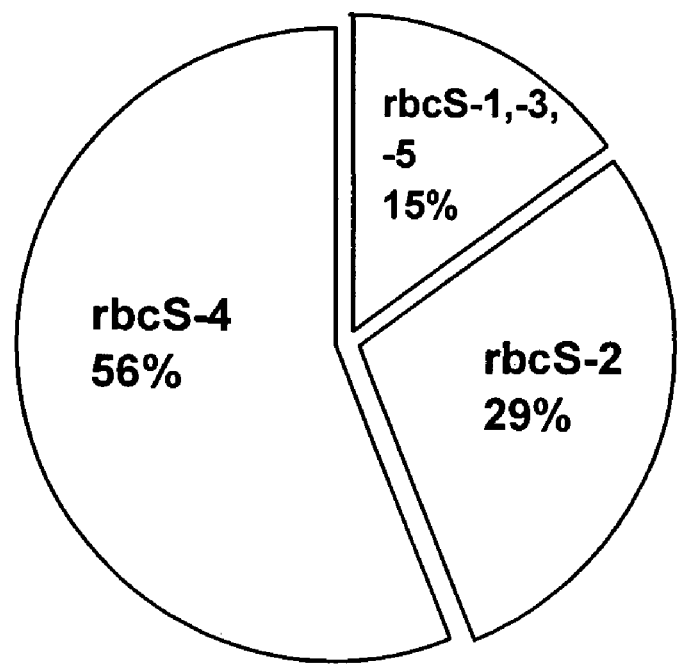
FIG. 1 illustrates relative quantities of different 3'UTR-type rbcS-genes in germinating seeds of *Brassica rapa*.

The present disclosure is related to transgene expression in germinating seedlings and sprouts. According to the present disclosure a strong protein expression is achieved by fusing the gene coding for the desired gene products with novel Rubisco promoters cloned from *Brassica rapa*. The novel promoters are selected from a group of Rubisco promoters derivable from rbcS genes, which have been selected from abundantly expressed rbcS genes in light-grown cotyledons of *Brassica rapa*.

The novel promoters consist essentially of SEQ ID NO: 1, SEQ ID NO: 2 and SEQ ID NO: 3. The promoter sequences are derived from native Rubisco promoters, but similar sequences can be prepared by other means including synthetic and semisynthetic methods.

The promoters according to the present disclosure were obtained by selecting and identifying genes, which were highly expressed in the developing cotyledons of light grown seedlings of *Brassica* species. 3'-UTRs of said highly expressed gene were isolated and characterized. Using said method three strong Rubisco promoters essentially comprising the sequences SEQ ID NO: 1, SEQ ID NO: 2 and SEQ ID NO: 3 were obtained and the capability of these promoters to direct gene expression in a spatiotemporal manner in developing cotyledons was characterized.

The Rubisco promoters are useful for designing recombinant DNA constructs or expression cassettes comprising SEQ ID NO: 1, SEQ ID NO: 2 or SEQ ID NO: 3 functionally fused in frame with reporter genes. In the present disclosure the term reporter gene means genes coding for homologous or heterologous proteins or other metabolic gene products. Reporter gene may code for any selected product, which is desired to be expressed in transgenic plant.

The reporter genes are exemplified by a β-glucuronidase (GUS) encoding gene (uidA) and a gene coding for human serum albumin (HSA). Also a synthetic gene consisting of part of immunoglobulin (Ig) G heavy chain and extra cellular domain of Tumor Necrosis Factor Receptor (TNFR) with or without ER-retention signal KDEL was used to exemplify a reporter gene. Furthermore, an antibody reporter gene is exemplified by heavy and light chains of human antibodies directed against hevein 1C2 antigen. One skilled in the art understands that these reporter genes are only examples and that any other reporter gene coding for a desired product may as well be used.

The recombinant constructs or expression cassettes according to the present disclosure are useful in transforming homologous and heterologous plants. The plant species are exemplified in this disclosure by *Brassica napus, Nicotiana tabacum* and *Camelina sativa*. Plant transformation procedures are familiar to those skilled in the art and therefore any other plant species can be transformed as well with the constructs according to the present disclosure. Applicable transformation systems include, but are not limited for example to the conventional *Agrobacterium* mediated transformation system. Especially transformation of *Camelina* plants according to a novel transformation system described in WO02/38779 and U.S. Ser. No. 10/416, 091 is included and hereby incorporated by reference.

The host plants were transformed with one or more of the above described DNA constructs or expression cassettes. Seeds from the transformed host plants, representing a zero generation, are collected and used for production of subsequent plant generations providing transgenic seeds. The transgenic seeds can be used for production of the desired proteins or gene products by allowing the seeds to germinate. When using the seeds for production in contained system, the germination can take place for example on buffered agar plates or in aerated vessels, such as appropriate fermentation equipment. The transgenic seeds provide an excellent nutritional source and the transgenic seeds may germinate into seedlings in a solution comprising mainly water, which may be appropriately buffered and contain growth hormones and other advantageous growth and germination promoting ingredients. Such cultivation enables production under sterile conditions and an easy recovery of the gene products.

In the present invention a method for producing the Rubisco promoters SEQ ID NO: 1, SEQ ID NO: 2 and SEQ ID NO: 3 is also provided. The method may be used to provide further promoters having similar useful properties as the Rubisco promoters of the present invention. The method thus enables production of new useful promoters for production of desired gene products from transformed seed in contained conditions. In the method the expression of light grown seedlings is evaluated and genes, which are highly expressed during the development of the cotyledon, are identified and their promoters are characterized. Promoters, which are capable of high expression levels in cotyledons during their development, are selected for designing DNA constructs and expression cassettes.

The following examples are meant to be descriptive and by no mean limiting the various embodiments of the present invention.

EXAMPLE 1

Rubisco mRNA Types Expressed in Cotyledons of Germinating *Brassica rapa* (*campestris*) Seeds A cDNA library was constructed in order to identify the most abundant types of Rubisco mRNA to be expressed in cotyledons of germinating *Brassica rapa* (*campestris*) seeds.

Total RNA was isolated from four days old *Brassica* seedlings, and a mRNA fraction was isolated from the total RNA preparations using oligo(d)T cellulose. A first strand cDNA was synthesized using oligo(d)T with M-MLV (Point mutant) reverse transcriptase. The next PCR step was carried out with a forward primer e3a 5'-CAUCAUCAUCAU-CAACCGTCAAGTCCAGTGCATCAGTTTCAT-3' (SEQ ID NO: 4) specific to the $3^{rd}$ exon of Rubisco SSU coding region and the reverse primer atu 5'-CUACUACUACU-ATTTTTTTTTTTTTTT-3' (SEQ ID NO: 5), an oligo(d)T derivative, specially designed according to CloneAmp procedure (Life Technologies). Both primers comprised on their 5'-terminal end several dUMP residues, which were destroyed by the enzyme UDG (Uracil DNA Glycosylase). The PCR step was carried out in 2 cycles, and subsequently the PCR product was digested by UDG and directly inserted into the linearized pAMP1 vector (Life Technologies) containing special protruding 3'-terminal ends compatible with protruding 3'-terminal ends of the RT-PCR products. The insert containing vector was transformed into competent *E. coli* strain XL-1. One hundred plaques were selected and analyzed. Inserts from plasmid DNA were amplified by PCR and the resulting PCR-products were sequenced. Relative number of separate colonies containing inserts of each type was calculated by the aid of sequence analysis.

Referring to FIG. 1, the sequence analysis of the cloned 3'UTRs showed striking quantitative differences between different Rubisco mRNA species. The sequence named '56' comprised 56% of all the Rubisco mRNA cloned. The other sequence named '29' comprised 29% of all the Rubisco mRNA. The rest 15% of the clones corresponded to the other types of Rubisco mRNAs.

The 29-type and 56-type sequences received from the cDNA library were compared to published sequences. The sequence alignments indicated that these Rubisco mRNAs are expressed from novel Rubisco promoters. The 29-type sequences are called rbcS-2 and the 56-type sequences are called as rbcS-4, respectively.

EXAMPLE 2

Cloning Rubisco Promoters Obtained from *Brassica rapa*

Based on the '56' and '29' type of sequences reverse primers were designed to be used in subsequent steps of promoter cloning.

Cloning of rbcs-2 Promoter

An EST-library was constructed first. The most common UTR found was UTR2, which was used to design reverse primers for Genome Walking step. Genomic DNA of *Brassica rapa* was digested by EcoRV, DraI, HincII, PvuI, SmaI and SspI and ligated to adapters (5'-GTAATACGACTCAC-TATAGGGCACGCGTGGTCGACGGCCCGGGCTGGT (SEQ ID NO: 6) and 5'-p-ACCAGCCC-NH$_2$-3'(SEQ ID NO: 7) to get six DNA libraries.

The next PCR amplifications (first and nested) were performed with adapter primer AP1 5'-GTAATACGACT-CACTATAGGGC-3' (SEQ ID NO: 8) and UTR2-specific L1 primer 5'-GGCCACACTTGACAATCCGATATAACAT-GCCTCA-3' (SEQ ID NO: 9).

Nested PCR was conducted with AP2 primer 5'-ACTAT-AGGGCACGCGTGGT-3' (SEQ ID NO: 10) and nested UTR2-specific L2 primer 5'-CAAATGGAAATGAAAT-GAGGTAG-3' (SEQ ID NO: 11).

The longest 900 bp product was obtained by using a DraI DNA library. This fragment was cloned into a pGEM3Zf(+) vector and sequenced. The sequence was compared with the sequences in GenBank database. The most homologous sequence found was *B. napus* rbcS (accession number X61097).

Near the 5'-end of one of the clones received (Rud3) was a 22 nt long stretch lacking from *B. napus* rbcS (beginning from 1037 nt of *B. napus* rbcS). Two reverse primers, RbNco and RbSiB, downstream from the putative transcription initiation site (based on the homology with X61097) and two forward primers, BNRb1 and BNRb3, based on X61097 homology, were designed. Full-length rbcS-2-gene was amplified using BNRb1 as a forward primer and UTR2-L2 as a reverse primer. Subsequently, two promoters of different length were amplified in nested PCRs using combinations of BNRb3 as a forward primer and RbSiB (with signal peptide) as a reverse primer, or BNRb3 as a forward primer and RbNco as a reverse primer (without signal peptide).

Cloning of rbcS-4 Promoter

Promoter cloning was conducted in several steps. Two reverse primers (for the first and nested PCRs) matching with the same sequences on the beginning of the first exons of three published Rubisco genes were used for the first step of Genome Walking.

Genomic DNA was isolated from *Brassica rapa* leaves and divided into six fractions. Each fraction was digested by one of six restricting enzymes (EcoRV, DraI, PvuII StuI, SspI, XmnI) and ligated with Genome Walking adapters (Clontech) mentioned above. Each restriction-ligation mixture represents a genomic DNA library.

The next step included two successive PCRs (first and nested) using adapter-specific AP1 and AP2 (forward) and gene-specific (reverse) primers. The PCR was started by using three different reverse primers, annealed to different parts of the first exon of Rubisco SSU gene in order to get the overlapping PCR products listed below.

```
(RbcS-RN:
5'-ACCCGGGCCCAGGAGAGCATAGAGGAAGCC- (SEQ ID NO: 12)
3',

RbcS-R1:
5'-CGGTGAATGGAGCGACCATCGTGGCTTGAG- (SEQ ID NO: 13)
3',

RbcS-R2:
5'-CTGTGAATGGAGCAACCATGGCCGCTTGAG- (SEQ ID NO: 14)
3'.
```

The six genomic DNA libraries described above produced amplification products after nested PCR. These products were directly cloned into pGEM-T-Easy vector (Promega) by TA-cloning. Colonies were screened by PCR using M13-universal and reverse primers. Colonies carrying plasmid DNA with insert were grown in liquid cultures and plasmid DNA isolated was used for sequencing analysis.

A total number of about ninety plasmid DNA insert-containing clones were analyzed. Based on data obtained from the sequencing analysis the sequences were divided into five groups according to sequence similarities. Three promoters were identified to be similar to the ones published in GenBank. Moreover, PCR using specially designed forward primers, specific to the cloned promoter regions, and reverse primers, specific for the '56'-type of 3'UTR (rbcS-4 type of 3'UTR) allowed identification of putative promoters having the 56 type of 3'UTR (rbcS-4 type of 3'UTR) in the genome. This promoter was called '56A'.

Figure 2A:
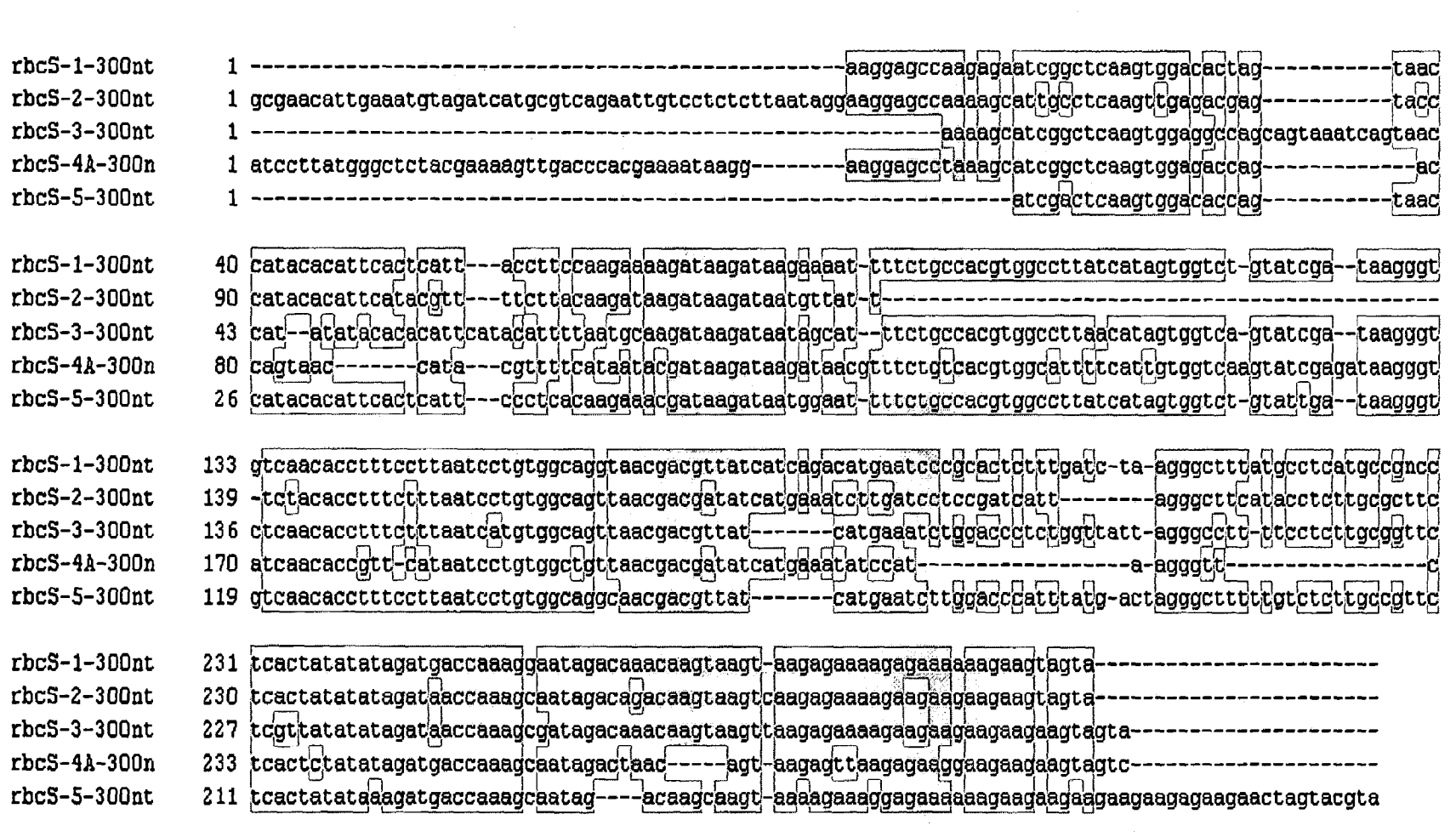
Figure 2B:
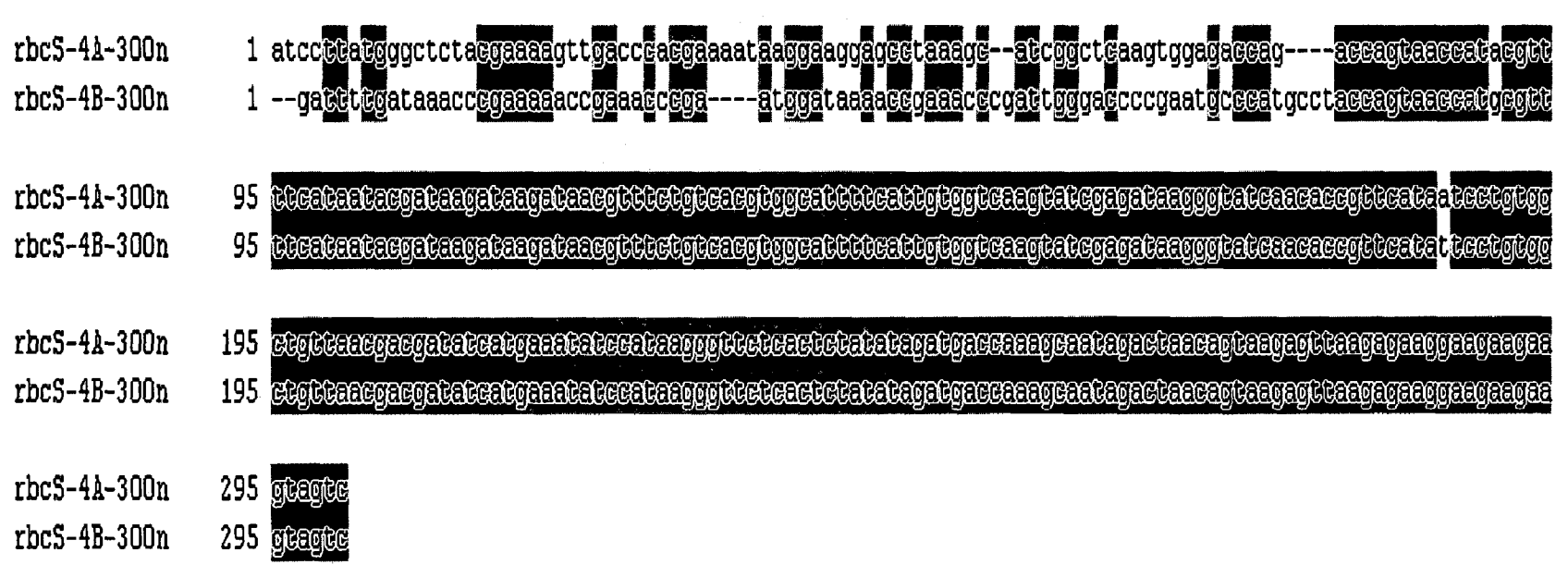

Based on the obtained sequences new reverse primers were designed to make next PCR step with the same forward primers (AP1, AP2) and the new reverse primers and using the same genomic DNA libraries. This procedure was repeated four times. The resulting sequences obtained after the fourth PCR cycle allowed us to design promoter-specific forward primers. The reverse primer was designed to include a special site for BpiI to create an NcoI-compatible restriction site. PCR using these primers and HiFi KOD polymerase enabled identification of the '56' type of promoter rbc-4A (SEQ ID NO: 1) among other sequences. By means of GenomeWalking techniques another promoter with the '56' type 3'UTR was found bound in the genome. This rbcS-4B promoter (SEQ ID NO: 2) was 98% similar to rbcS-4A on the length of about 230 nt region in (1953-2175 nt SEQ ID NO: 1 and 794-1016 nt in SEQ ID NO: 2), but distal parts of rbcS-4A and rbcS-4B showed less than 40% similarity. FIG. 2B gives an alignment of −267 to +33 nt regions of these two promoters. RbcS-4B promoter was also cloned with proof-reading KOD polymerase and its functional activity was studied further.

By using the same approach, totally four steps of Genome Walking were applied to clone the rbcS-4A promoter and two steps were applied to clone rbcS-1, rbcS-3 and rbcS-5 promoters (SEQ ID NO: 21, SEQ ID NO: 22 and SEQ ID NO: 23, respectively). After the final step of Genome Walking whole length promoters were cloned using the proof-reading Pfu DNA polymerase enzyme. The 3'-terminal ends of the cloned promoter sequences were designed so that they can be ligated with reporter genes. GenBank BLAST system was used to analyze the promoter sequences obtained. Brassica promoters having accession numbers X55937 and X75334 showed similarity of up to 98-99% with rbcS-3 and rbcS-5 promoters, respectively. All the promoters cloned and known were compared to each other by computer alignment program. This analysis showed that the promoters have similar parts located mostly in about 300 nt region. Alignment of 300 bp length proximal parts of these rbcS promoters (excluding rbcS-4B (see below) is presented in FIG. 2A.

The Genome Walking data showed that there were two partially different rbcS-4 (called rbcS-4A and rbcS-4B) promoters connected to the same 3'UTRs and being very similar on the last 230 bp on their 3'-terminal ends (FIG. 2B) (rbcS-4A is SEQ ID NO: 1; rbcS-4B is SEQ ID NO: 2). On the other hand, the distal parts of the promoters show the same low level of homology (40%) as they show in alignment with other Rubisco promoters.

Figure 2C:
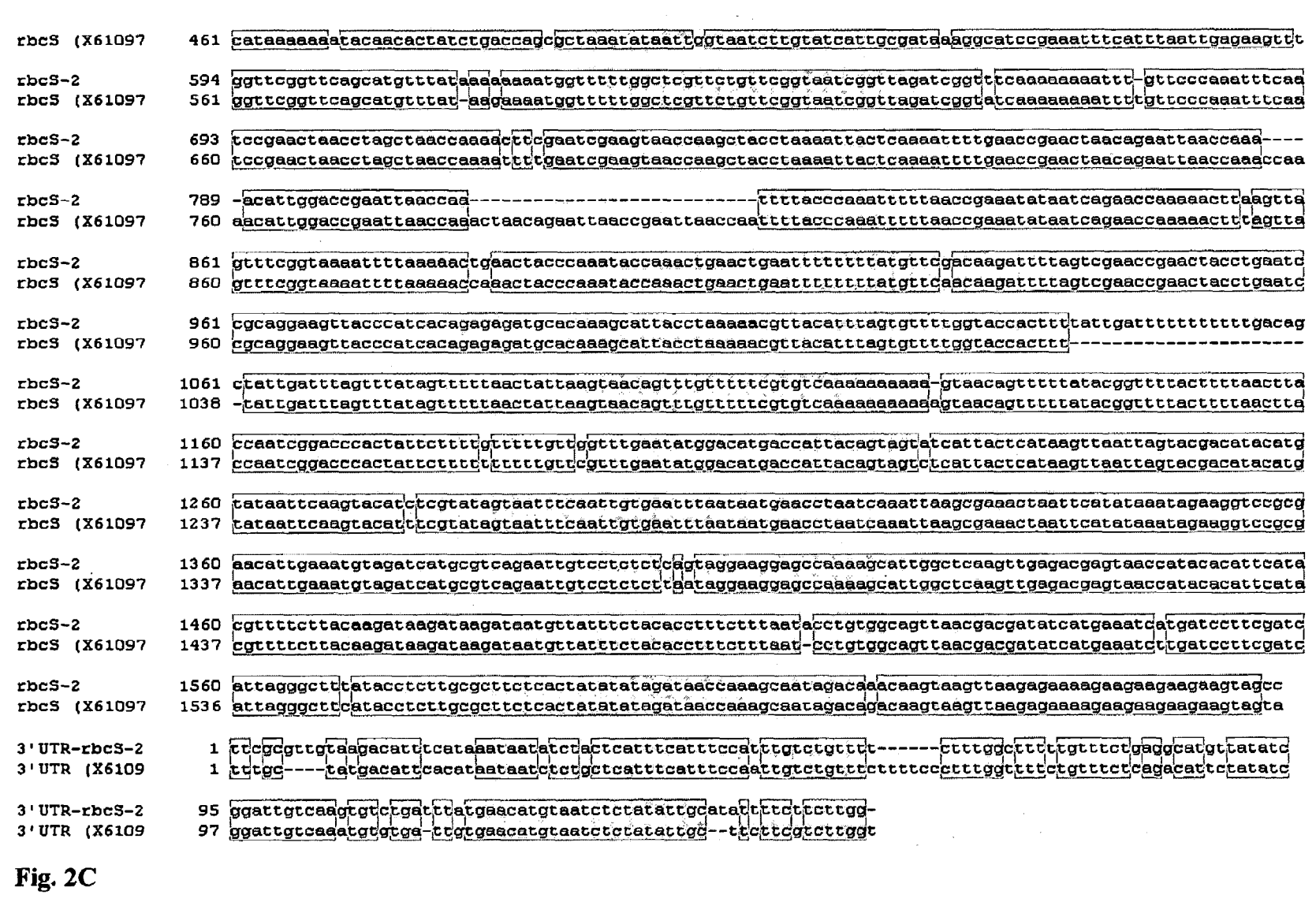

Alignment of one of the published Brassica napus Rubisco promoter (accession number X61097) (SEQ ID NO:33) with rbcS-2 (SEQ ID NO: 3), demonstrates some differences (91% similarity) between them (FIG. 2C). There are also differences in 3'UTR regions. Therefore, these two promoters are not the same ones and probably diverged during evolution or selection process of rbcS gene family in Brassica species.

Figure 3:
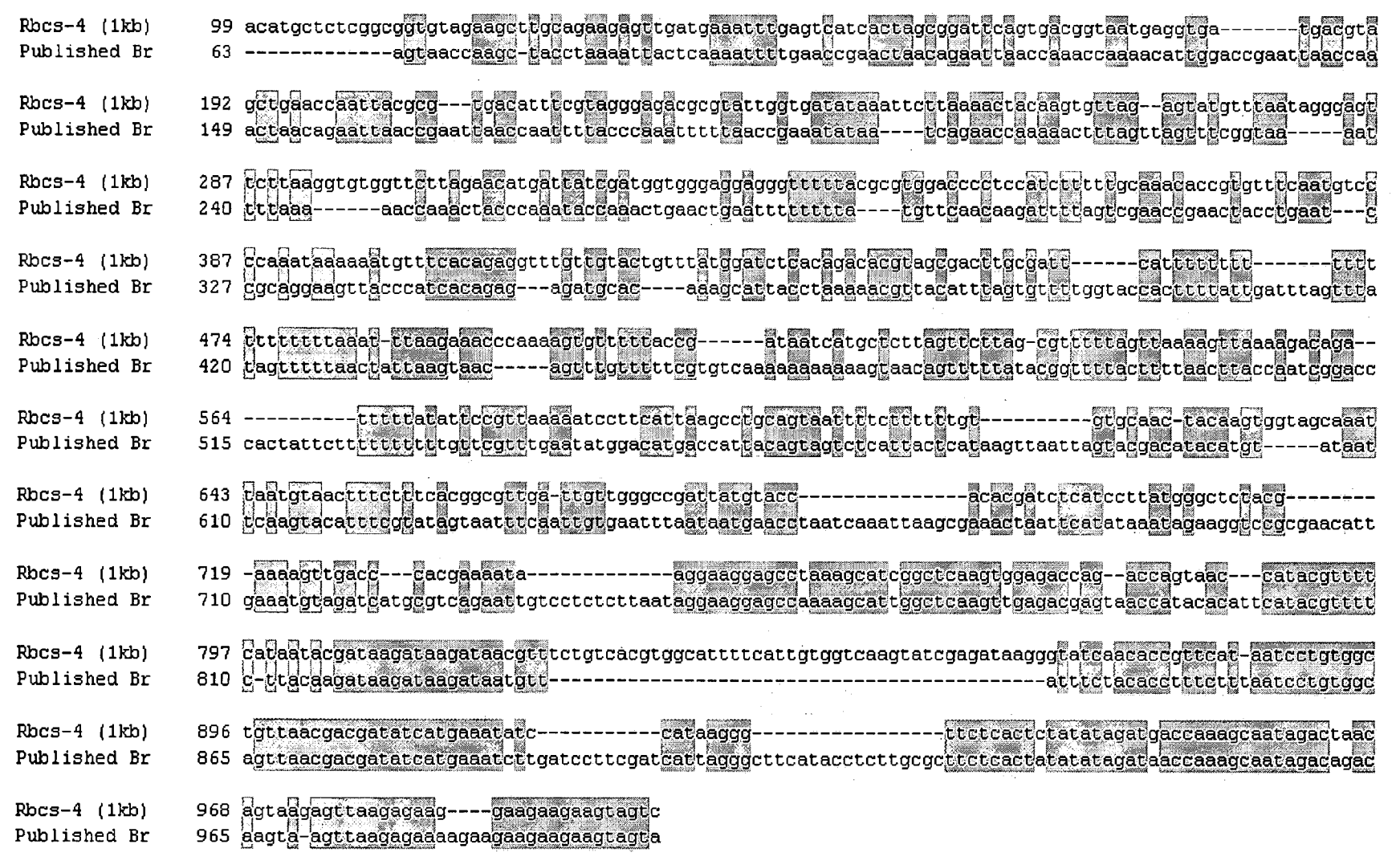

Referring to FIG. 3 alignment of rbcS-4A promoter sequence and published Brassica rubisco promoter (X61097) revealed dissimilarity of 52%.

Figure 4:
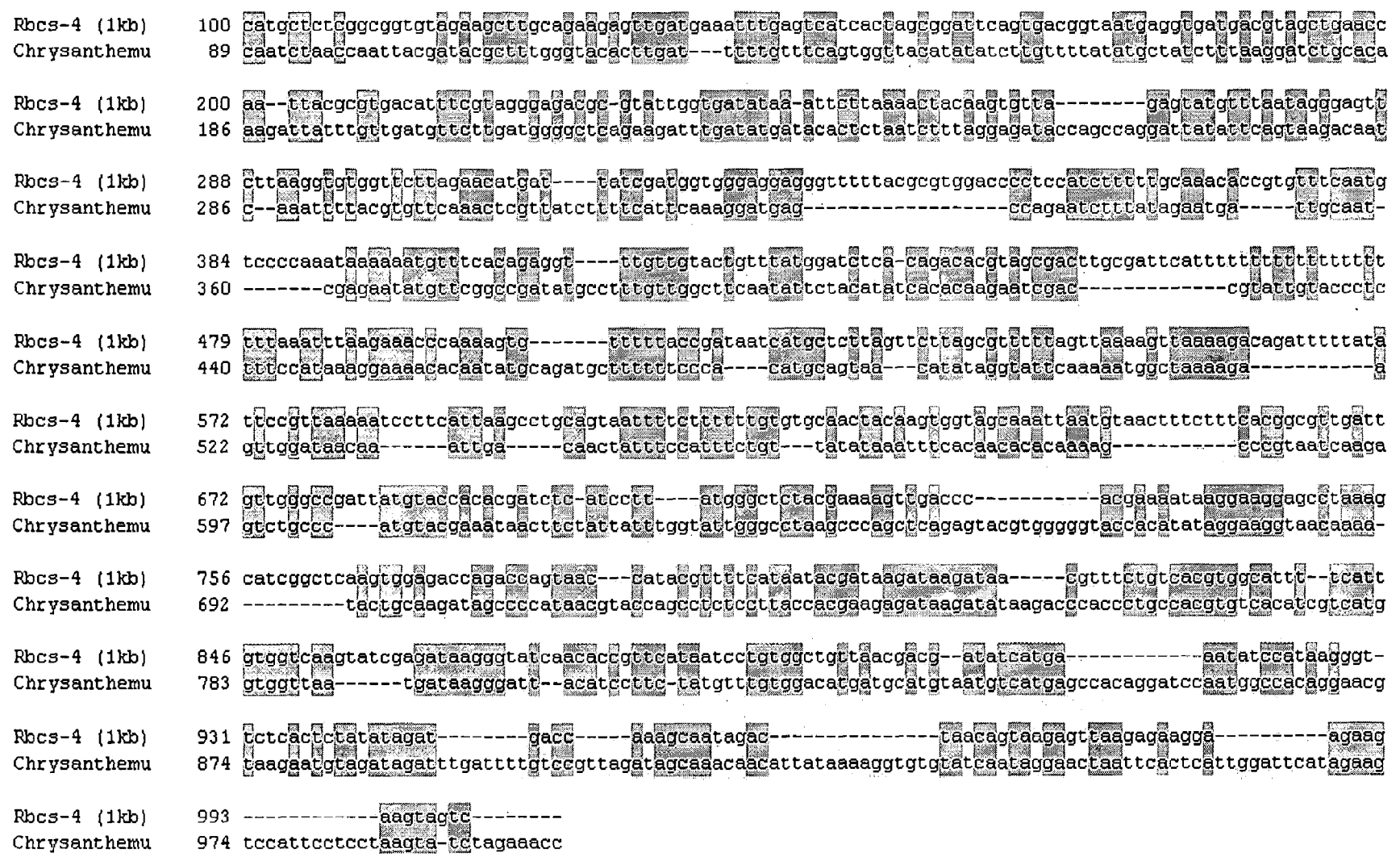

Similarly, referring to FIG. 4 alignment of rbcS-4A promoter sequence with the published Chrysanhetmum rbcS-1 promoter (AY 163 904) (SEQ ID NO: 35) revealed dissimilarity of 57%.

Figure 17:
FIG. 17 illustrates homological regions of the sequence of Rbcs-4A (SEQ ID NO: 1) promoter and *Brassica* sequence published in *Brassica* genome project with accession number BH 484651 and cDNA sequence (accession number CD811761) of *Brassica napus*.

Markedly, there are only three stretches in rbcS-4A promoter (1007-1440 nt, 1776-1950 nt and 1959-2175 nt) that have a quite high homology (similarity of about 93%) with Brassica genome project database (FIG. 17). Accession number BH484651 represents genomic clone of Brassica oleracea and CD811761 represents cDNA clone of Brassica napus. No other parts of the rbcS-4A promoter sequence are found in any database including Brassica genome project.

Clearly the nucleotide sequences of rbcS-2 (SEQ ID NO: 3) and rbcS-4A (SEQ ID NO: 1) and rbcS-4B (SEQ ID NO: 2) are novel and useful as described in this disclosure.

EXAMPLE 3

Fusion-constructs rbcS-4A-GUS, rbcS-4A-HSA, rbcS-4B-GUS, rbcS-2-GUS, rbcS-2-HSA, rbcS-2-Ab(L+H)-1C2, rbcS-4A-Ab(L+H)-1C2, rbcS-2, TNFR-Fc and rbcS-4-TNFR-Fc The promoters were amplified with reverse primers to get NcoI-compatible restriction site on their 3'-terminal ends. Vector pCAMBIA1301 (CAMBIA) containing GUS gene with NcoI site on its 5'-terminal end was used. HSA fusion constructs were designed in a pBIN19-based plasmid pGPTV with an inserted HSA gene (SEQ ID NO: 15). RbcS-4A and rbcS4B were cut out by BpiI, HindIII. RbcS-2 was cut out by NcoI, HindIII. RbcS- 4A, rbcS-4B, and rbcS-2 were cloned into pCAMBIA1301or pGPTV vectors opened by NcoI, HindIII. The terminators used for these constructs were as follows: nos-terminator in GUS-containing pCAMBIA1301 vector, and rbcS-4 type of 3'UTR plus part of known Brassica rapa rbcS terminator from GenBank was used in LISA-containing pGPTV plasmids.

Constructs Rbcs-2-Ab(L+H)-1C2 and RbcS-4-Ab(L+H)-1C2 contain the same antibody regions and the same terminator (polyA) signal from the natural Brassica rubisco RbcS-4 gene (directly from the genome). The antibody protein molecule was originally developed against hevein 1C2 antigen. RbcS-2-Ab(L+H)-1C2 consists of RbcS-2 promoter, light chain (anti-hevein 1C2) (SEQ ID NO: 16) coding region, rbcS-4 terminator (SEQ ID NO: 17), another RbcS-2 promoter, heavy chain (anti hevein 1C2) (SEQ ID NO: 18) coding region, and another Rbcs-4 terminator. The RbcS-4-Ab(L+H)-1C2 construct consists of Rbcs-4 promoter, light chain (anti-hevein 1C2) (SEQ ID NO: 16) coding region, RbcS-4 terminator, another RbcS-4 promoter, heavy chain (anti-hevein 1C2) coding region (SEQ ID NO: 18), and another RbcS-4 terminator.

For the constructs Rbcs-2-Ab(L+H)-1C2 and RbcS-4-Ab(L+H)-1C2, the rbcS-2 and rbcS-4 promoters were cut by SalI, HindIII and ligated with pVK1-CHC(constant heavy chain)-rbcS-4-terminator, digested with SalI, and HindIII providing the pVK1-RbcS-2(Rbcs-4A)-promoter-CHC-RbcS-4-terminator. RbcS-4 terminator was originally cloned with CHC by BsiWI, EcoRI. Variable heavy chain region of 1C2 antibody (VH-1C2) was cut out by BpiI, Bsp120I and cloned into a pVK1-Rbcs-2(Rbcs-4)-promoter-CHC-RbcS-4-terminator vector by the same sites. The resulting plasmid was the plasmid containing whole H (heavy) chain unit. The same strategy was used to get the whole L (light) chain unit.

L chain unit was then cloned into pCAMBIA1301 vector from where the 35S-GUS region was removed. This was pCAMBIA1301-L-chain. In the final step the H-chain unit was inserted into pCAMBIA1301-L-chain vector to get the final pCAMBIA1301-H-L. The plasmid was used for plant transformation using *Agrobacterium*-mediated strategy.

Ig-TNFR (ENBREL) construct contains rbcS-2 or rbcS-4 promoters, TNFR (tumor necrosis factor receptor) part (489 nt) (SEQ ID NO: 19) comprising the IgCHC part (CR2 and CH3 domains) and terminators. TNFR part was cloned directly from human mRNA by reverse transcription followed by PCR, ligated into pGEM-T-Easy plasmid by TA-cloning procedure and sequenced from both directions with M13-universal and reverse primers. Ig CHC part was obtained by PCR and sequenced thereafter. Cloning strategy included ligation of Ig CHC part by BsiWI site and introducing promoter into pVK1 plasmid (pUC19 derivative), containing rbcS-4-terminator. Then TNFR part digested by BsmB1 was introduced into this plasmid, and whole the insert was re-cloned into big pCAMBIA1300 or pCAMBIA2300 plasmids.

IgCHC part was obtained in two variants. The first was without any changes in its 3' end and the second one contained KDEL signal in its 3' end. This signal is 12 nt long sequence AAAGACGAGCTG (SEQ ID NO: 24) and is introduced just before the STOP-codon. Several terminators were used in the Ig-TNFR constructs. One was rbcS-4 terminator (about 500 nt) being the same as used in antibody constructs. Another terminator was a longer version of the rbcS 4-terminator (being about 2kb). Still another terminator used was from *Arabidopsisis* VSP1 (vegetative storage protein-1 gene), the part situating right behind the STOP codon and before cleavage site was used and was connected with part of rbcS- 4 (SEQ ID NO: 20). In some of the constructs one or two MAR (matrix attachment regions) sequences (about 2kb) were also introduced. In case the construct contained two MAR sequences they were introduced before the promoter and after the terminator.

EXAMPLE 4

Plant Transformation

To exemplify the functionality of the novel promoters according to this disclosure, we transformed plants of *Brassica* species, *Nicotiana tabacum* plants and *Camelina sativa* plants. One skilled in the art is able to transform plants of other species.

*Brassica* plants were transformed with *A. tumefaciens* strain LBA4404 carrying the pCAMBIA1301 or pGPTV-HPT binary vectors by leaf disk inoculation. Tobacco plants *Nicotiana tabacum* cv. Samsung were transformed with *A. tumefaciens* strain LBA4404 carrying pGPTV-HPT binary vectors by leaf disc inoculation. Putative transformants were selected on 30 mg/l hygromycin. Positive lines were transferred to the greenhouse for further studies

*Camelina* plants were transformed with *A. tumefaciens* strain C58 (helper plasmid pGV3850) carrying the pCAMBIA1300 binary vectors by leaf disc inoculation. Putative transformants were selected on 20 mg/l hygromycin. Positive lines were transferred to the greenhouse for further studies.

EXAMPLE 5

Quantitative GUS Assay for Expression Analysis

The assays were carried out with tobacco leaves or *Camelina* seedlings. Fresh plant material was mechanically disrupted in Tris-buffer, containing 2-ME. Protein concentrating in extracts was determined using Bio-Rad assay. GUS activity was determined in spectrophotometer using p-nitrophenyl-β-D-glucuronide as a substrate for the enzymatic reaction. Incubation was 30 min at +37° C. and developed color was measured in spectrophotometer at 450 nm wavelength. Non-transgenic plants were used as negative controls.

EXAMPLE 6

Expression Analysis of mRNA with Real-Time RT-PCR and Northern Analysis

Total RNA isolated from cotyledons of germinating *Brassica* or *Camelina* seeds or tobacco leaves were reverse transcribed with gene specific reverse primers. The reverse primers were designed for non-similar parts of all the 3'UTR known as well as for HSA, GUS, heavy and light chains of anti-hevein 1C2 antibody and the third exon of Rubisco SSU coding region. cDNA obtained was used for Real-time PCR step using forward and the same reverse primers.

Real-Time procedure was conducted on API7000 machine mainly according to the manual using SYBRgreen quantitative variant of the method. The passive reference dye was ROX. The calibration curves were constructed using PCR products amplified from genome and purified with the same primers as in Real-Time process. The result was expressed in number of molecules per 1 μg of total RNA sample originally taken.

For the Northern analysis total RNA was isolated from plant material and run on agarose gel and transferred onto the membrane. Then RNA was cross-linked to the membrane by short exposure to UV light. Next step is hybridization with specific RNA probe, synthesized in vitro from bacterial T7 or SP6 promoters, Hybridization was going on overnight at optimal temperature, specially optimized for every probe. After washing, the membrane is undergone to incubation with antibodies recognizing DIG-labels on the probe. The amount of the RNA probes (i.e. specific mRNA) was detected by enhanced chemiluminescence using negative and positive controls (varying concentrations), allowing determination of the amount of specific mRNA in the experimental sample.

EXAMPLE 7

Expression Levels of Rubisco Genes and Total Rubisco mRNA in Germinating Seeds Increases Toward End of Cotyledon Development The total RBCS mRNA content in constant light conditions increased during the first 3-4 days and remained on a high level for the next 5 to 7 days (FIG. 16).

In order to determine the expression levels of different Rubisco genes and also total Rubisco mRNA production in germinating *Brassica napus* seeds we measured the amount of total Rubisco mRNA in seeds on 0, 1, 2, 3 and 4 day of germination in constant light conditions by Real-Time PCR. This is illustrated in FIG. 9.

The quantitative data shown in FIG. 9 (first column), demonstrates the amount or number of Rubisco mRNA molecules in 1 μg of total mRNA per an average sample. Clearly, the amount of mRNA molecules increased from day 0 to day 4, showing the highest amounts on the $4^{th}$ day. On $4^{th}$ day of germination the amounts of RBCS mRNA determined in most of the samples were about $4-7 \times 10^7$ molecules per 1 μg of total mRNA.

EXAMPLE 8 rbcS-4 Type of RBCS mRNA is the Most Prevalent and Active Type of mRNA at the Stage of Germinating Seeds of Plant Development, But rbcS-2 Reaches its Highest Activity Faster The amount of different types of RBCS mRNAs was analyzed by the Real Time process described above. The expression levels of rbcS-2, rbcS-3, rbcS-4 and rbcS-5 were determined on 0-4$^{th}$ day of *Brassica napus* seed germination by using primers specific to non-similar parts of 3'UTRs of those mRNA species (FIG. 5). Forward primers were designed so that they have longer right part, corresponding to specific 3'UTR type. The shorter left part of each primer corresponds to the end of the RBCS coding region. This left part helps to increase length and therefore Tm of the primer, but does not disturb the specificity of it (FIG. 5).

Data summarized on FIG. 9 (columns 3-6), demonstrates dramatic differences in the expression levels. The most abundant type during the four days of seed germination was rbcS-4 RBCS mRNA, but as we have already noticed above there are at least two rbcS genes driven by the partially similar promoters (rbcS-4A and -4B; SEQ ID NO: 1 and SEQ ID NO: 2, respectively) and connected to the same 3'UTR (rbcS-4 type of 3'UTR). This may mean that each rbcS-4 gene can contribute to the sum activity of the gene. But according to quantitative GUS expression data obtained from rbcS-4B-GUS transgenic tobacco plants (FIG. 10) the activity of the promoter is very low and doesn't seem to have remarkable influence on total amount of mRNA containing rbcS-4 type of 3'UTR.

The data presented here clearly demonstrates the prevalence of rbcS-4 type of RBCS mRNA on the later stage of germinating seeds of plant development.

Referring now to results shown in FIG. 9 Real-Time PCR showed that rbcS-4 promoter was more active at the fourth day of germination than any other Rubisco promoter examined. The expression level of different RBCS genes followed different kinetics: for example at third day rbcS-2 (SEQ ID NO: 3) and rbcS-3 (SEQ ID NO: 22) were more active than rbcS-4 and rbcS-5 (SEQ ID NO: 23). These characteristics are extremely important when selecting a promoter for a production method of foreign proteins or other desired gene products to be produced in germinating seeds or sprouts.

Unstable transgenic proteins may degrade quite fast because of enhanced protein mobilization capacity of plant cells in tissues of germinating seeds. When using a promoter such as rbcS-4 with delayed kinetic of activity, there are more chances to protect accumulation of transgenic protein product from the action of lytic vacuoles. Moreover, additional benefits of using rbcs-4A in transgenic constructs arise from the fact that this is the strongest promoter out of the four promoters analyzed at later stages of seed germination. On the other hand, using rbsc-2 would give stronger expression in earlier phase of germination and this can be of benefit for some applications.

FIG. 13 compares the accumulation of HSA mRNA in germinating *B. napus* seeds transgenic for rbcS-4-HSA or for (rbcs-2-HSA)×2. The (rbcS-2-HSA)×2 is a variant of rbsS-2-HSA where 2 units of rbcS-2 are arranged in tandem. It is evident that HSA mRNA begins to accumulate earlier in the seeds transgenic for (rbcS-2-HSA)×2. On the other hand HSA mRNA in rbcS-4-HSA transgenic plants starts to accumulate later but the amount accumulating is somewhat bigger. As seen from FIG. 9, the kinetics of rbcs-4 promoter activity is more delayed than that of rbcS-2, and therefore it is evident that both of the promoters are functional even when in non-native conditions.

EXAMPLE 9

Heterologous and Homologous Transgenic Plants Harboring rbcS-2 and rbcS-4 Promoters for Production of Desired Gene Products rbcS-2 (SEQ ID NO: 3) and rbcS-4 (SEQ ID NO: 1 and SEQ ID NO: 2) promoters were used for plant transformation experiments with *Brassica*, tobacco and *Camelina* plants to determine the 'promoter strength' and also to compare the expression levels in homologous and heterologous systems (i.e. plants transformed with a construct containing a promoter from the same or a different species).

The promoters were amplified with reverse primers to get NcoI-compatible restriction site on their 3' ends. pCAMBIA1301 vector (CAMBIA) containing GUS gene with NcoI site on its 5' end designed as described in Example 2 were used.

Promoters rbcS-2 (SEQ ID NO: 3), rbcS-4A (SEQ ID NO: 1) or rbcS-4B (SEQ ID NO: 2) containing constructs inserted in the genome of *Brassica* represent homologous system, and the insertion of the same constructs in tobacco and *Camelina* plant's genome represent heterologous system. Recombinant constructs containing rbcS-2 or rbcS-4 promoters fused in frame with reporter genes were designed as described in Example 3 and transformed into plants as described in Example 4.

mRNA expression data of transgenic *Brassica* plants containing rbcS-4-GUS or rbcS-2-GUS is presented in FIG. 7. The mRNA expression level of reporter gene was measured by Real-Time PCR from cotyledons of seeds of transgenic *Brassica* plants germinated for 4 days.

Referring to data presented in FIG. 7 it can be seen that expression of transgene (GUS) mRNA in both plant transformants is about 5-6 times less than the expression of corresponding native rubisco gene (rbcS-2 or rbcS-4A). Furthermore expression level of native rbcS-4A gene in transgenic plant corresponds to the one in non-transgenic plant (FIG. 9), but the expression level of native rbcS-2 gene in rbcS-2 transgenic plant is less than that in non-transgenic plant. The result probably is related to higher silencing dependency of rbcS-2 promoter in homologous plant.

For tobacco transformation experiments rbcS-2-HSA and rbcS-4A-HSA constructs were used and seven HSA-producing plant lines for each of them were received. The mRNA expression level of HSA gene determined on 5th day of transgenic tobacco seed germination demonstrate about the same level of expression in both types of these plant lines (FIG. 8). The tobacco transformation experiments show clearly that there is no significant difference between the rbcS-2 and rbcS-4 promoters strength, but both of them are expressing in heterologous system.

Transgenic *Camelina* and tobacco plants harboring rbcS-2-GUS, RbcS-4-GUS, RbcS-2-TNFR-Fc-56UTRshort, RbcS-2-TNFR-FcKDEL-56UTRshort, RbcS-4-TNFR-Fc-56UTRlong, or RbcS-4-TNFR-FcKDEL-56UTRlong constructs were obtained and analyzed further. The results are shown in FIGS. 18 A and B. Determination of GUS-activity demonstrates that enzyme activity level in rbcS-2 (rbcS-4)-GUS transgenic plants is higher than in plants carrying conventional 35S-GUS construct used here as positive control. Northern data is available for some TNFR-Fc-harboring *Camelina* and tobacco plants. The expression level for RbcS-4-TNFR-Fc is comparable with that of native rbcS genes (in Brassica about 50-100 pg/μg of total RNA for whole RBCS gene family).

EXAMPLE 10

Protein Expression in Transgenic Plants

Figures 10, 11:
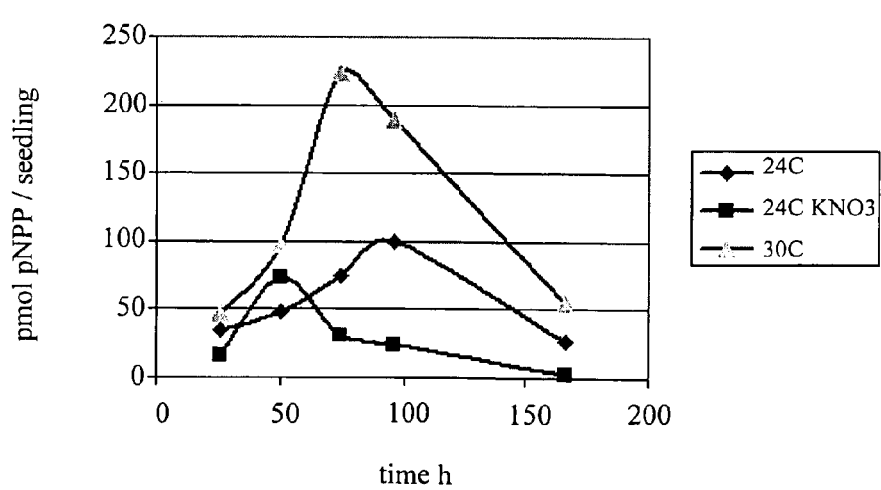
FIG. 10 illustrates the GUS expression in transgenic tobacco plants transformed with rbcS-4B-GUS (Rubisco promoter sequence SEQ ID NO: 2). Plants transformed with a gene encoding GUS under the Cauliflower Mosaic Virus (CaMV) 35S promoter (35S-GUS) were used as controls.
FIG. 11 illustrates the GUS expression under Rubisco promoter rbcS-4A (SEQ ID NO: 1) during germination of *Brassica* seeds in constant light at 24° C. or 30° C.

A construct comprising GUS gene coding region was linked to the Rubisco promoter rbcS-4A and transformed into an oilseed rape (*Brassica rapa*) plant using *Agrobacterium* mediated transformation. Transgenic plants were grown in greenhouse until seeds were produced. Seeds of transgenic plants were allowed to sprout in 20° C. aerated water; 24° C. aerated 20 mM KNO₃ water or in 30° C. aerated water. After variable times of cultivation expressed GUS protein was isolated from the sprouts by homogenization in appropriate buffer and centrifugations. Specific GUS activity was determined by spectrophotometer (FIG. 11). Clearly, GUS activity per sprout was highest after 72 hours of cultivation using KNO₃ in the growth medium.

Figures 15, 16A, 16B:
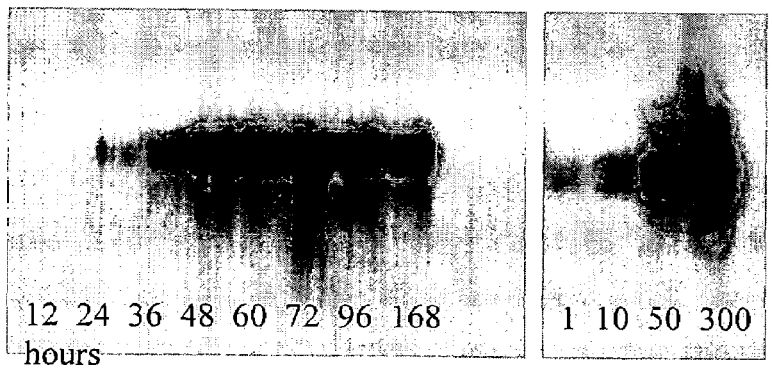
FIG. 15 illustrates the GUS activity in transgenic tobacco plants transformed with constructs containing GUS as the reporter gene and either full length rbcS-2 ((SEQ ID NO: 3) promoter (1.6 kb) or a truncated versions of the promoter. Plants transformed with 35S-GUS construct were used as a positive control.
FIG. 16A is a Northern blot showing the synthesis of Rubisco SSU mRNA in *Brassica* seedling after sprouting in an airlift tank for 12 to 168 hours.
FIG. 16B shows unlabelled Rubisco RNA of germinating *Brassica* seedlings produced by in vitro transcription when loaded on the same filter as the control. The amount of control RNA is indicated in pg.

Protein expression of transgenic *Brassica napus, Camelina sativa* and tobacco plants carrying HSA under the control of rbcS-2 or rbcS-4 were also analyzed. Similarly, plants carrying tandem construct of RbcS-2-HSA were analyzed. Protein expression was analyzed from sprouts that germinated at constant light and 24° C. temperature for four days. FIG. 15 shows the data as % of total soluble protein. It is evident that plants carrying the tandem construct have higher expression levels of the protein than plants carrying single construct. Furthermore, it is evident that protein expression is higher under rbcs-4 promoter than under rbcS-2 promoter. The tandem construct having two rbcS-2-HSA constructs is an example of a multiple construct according to the present invention and one skilled in the art would be able to transform plants with more than two constructs in tandem as well. Similarly, one skilled in the art would be able to use tandem constructs having rbcS-4 as the driving promoter to obtain higher protein contents.

Protein expression of transgenic *Camelina sativa* and tobacco plants carrying TNFR constructs was analyzed. The results are shown in FIG. 18 B.

EXAMPLE 11

In Order to Provide Maximal Activity the Rbcs Promoter has to be of Full Length

Figure 6:
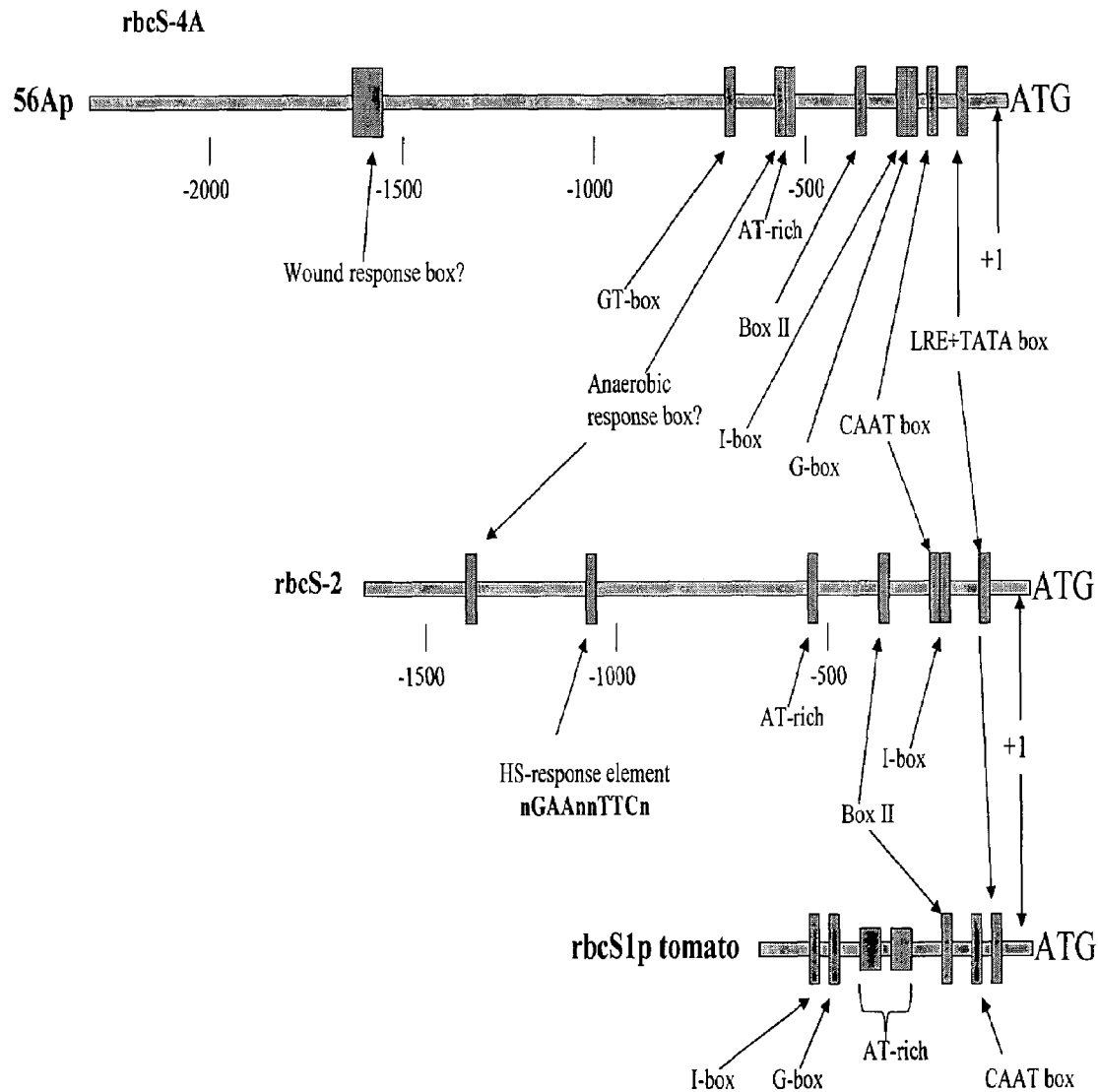
FIG. 6 is a scheme of consensus regulatory elements found in rbcS-2 (SEQ ID NO: 3) and rbcS-4A (SEQ ID NO: 1) promoters.

Truncated versions of rbcS-2 promoter were cloned, (0.3 and 0.6 kb length) in fusion constructs with the reporter uid A gene encoding GUS. Tobacco plants were transformed by *Agrobacterium* carrying these constructs and the GUS activity was measured from leaves of adult tobacco plants. The data obtained was compared to data obtained from the analysis of high-expressing adult tobacco plants carrying rbcS-2 (1.6 kb) or 35S promoters connected to the GUS gene. The results as shown in FIG. 15 clearly demonstrate decrease of registered GUS activity due to reduction of the length of the promoter. Therefore it is evident that distal regions of the rbcS-2 promoter contain essential regulatory elements supporting basal (non-inducible) promoter activity. Comparative analysis in silico of known tomato rbcS-1 promoter and our cloned *Brassica* rbcS-2 and rbcS-4A promoters enables to find similar consensus regulatory elements in all of them (FIG. 6). It is clear that most of the known boxes are located in the −500-600 nt region. It could be suggested that those distal parts of the promoters may have some cryptic regulatory elements or they may participate in the promoter action because of possible occurring of MAR (Matrix Attachment Region) sites, for example, in 5' regions of rbcS-4A (computer MAR prediction analysis).

What is claimed is:

1. A rubisco promoter isolated from *Brassica rapa* light grown seedlings, said promoter having capability to direct gene expression into developing cotyledons and said promoter comprising the nucleotide sequence of SEQ ID NO: 3.

2. An expression cassette comprising a Rubisco promoter of SEQ ID NO: 3 and further being operably linked to a heterologous nucleic acid sequence encoding a desired gene product.

3. The expression cassette according to claim 2, wherein the heterologous nucleic acid sequence is synthetic.

4. The expression cassette according to claim 2, wherein the heterologous nucleic acid sequence encodes human serum albumin.

5. The expression cassette according to claim 2, wherein the heterologous nucleic acid encodes an antibody.

6. Transgenic seedlings for production of desired products, said transgenic seedlings comprising at least one expression cassette according to claim 2.

7. Transgenic seedlings according to claim 6, wherein said transgenic seedlings comprise two expression cassettes.

8. Transgenic seedlings according to claim 6, wherein the seedlings are *Camelina sativa* seedlings.

9. A transgenic plant, comprising at least one expression cassette according to claim 2.

10. A transgenic seed comprising at least one expression cassette according to claim 2.

11. An isolated polynucleotide comprising the sequence of SEQ ID NO: 3.

* * * * *